US009707466B2

(12) United States Patent
Bleich et al.

(10) Patent No.: US 9,707,466 B2
(45) Date of Patent: Jul. 18, 2017

(54) SYSTEMS AND METHODS FOR COORDINATING MUSCULOSKELETAL AND CARDIOVASCULAR OR CEREBROVASCULAR HEMODYNAMICS

(71) Applicant: Pulson, Inc., Palo Alto, CA (US)

(72) Inventors: Jeffery L. Bleich, Palo Alto, CA (US); Paul Mannheimer, Los Altos, CA (US)

(73) Assignee: Pulson, Inc., Palo Alto, CA (US)

( * ) Notice: Subject to any disclaimer, the term of this patent is extended or adjusted under 35 U.S.C. 154(b) by 0 days.

(21) Appl. No.: 15/384,268

(22) Filed: Dec. 19, 2016

(65) Prior Publication Data

US 2017/0095721 A1  Apr. 6, 2017

Related U.S. Application Data

(63) Continuation of application No. 14/553,732, filed on Nov. 25, 2014, now Pat. No. 9,522,317, which is a
(Continued)

(51) Int. Cl.
*A63B 71/06* (2006.01)
*G09B 19/00* (2006.01)
(Continued)

(52) U.S. Cl.
CPC ............ *A63B 71/06* (2013.01); *A61B 5/0205* (2013.01); *A61B 5/0456* (2013.01);
(Continued)

(58) Field of Classification Search
CPC . A63B 71/06; A63B 22/0023; A63B 22/0235; A63B 22/0605; A63B 24/0062;
(Continued)

(56) References Cited

U.S. PATENT DOCUMENTS 2,690,174 A 3/1949 Fuchs
3,303,841 A 2/1967 Dennis
(Continued)

FOREIGN PATENT DOCUMENTS

EP 2744403 6/2014
EP 2967401 1/2016
(Continued)

OTHER PUBLICATIONS

International Preliminary Report on Patentability and Written Opinion, received in PCT/US2012/051511, mailed Feb. 25, 2014.
(Continued)

*Primary Examiner* — Timothy A Musselman
(74) *Attorney, Agent, or Firm* — Aurora Consulting LLC

(57) ABSTRACT

Described herein are methods for determining a target musculoskeletal activity cycle (MSKC) to cardiac cycle (CC) timing relationship. The method may include detecting a first characteristic of a signal responsive to a CC timing of a user that repeats at a frequency that corresponds to a heart rate of the user; detecting a second characteristic of a signal responsive to a rhythmic musculoskeletal cycle activity (MSKC) timing of the user that repeats at a frequency that corresponds to the MSKC rate of the user; determining a value representative of an actual timing relationship between the first characteristic and the second characteristic; detecting a third characteristic of a signal corresponding to a physiological metric that varies with the actual timing relationship between the first and second characteristics; and determining a target value representative of a preferred timing relationship between the first and second characteristics.

22 Claims, 15 Drawing Sheets

Related U.S. Application Data continuation-in-part of application No. 13/589,073, filed on Aug. 17, 2012, now Pat. No. 8,961,185.

(60) Provisional application No. 61/525,689, filed on Aug. 19, 2011.

(51) Int. Cl.

| | |
|---|---|
| *A63B 22/00* | (2006.01) |
| *A63B 22/02* | (2006.01) |
| *A63B 22/06* | (2006.01) |
| *A63B 24/00* | (2006.01) |
| *A63B 69/00* | (2006.01) |
| *A61B 5/0205* | (2006.01) |
| *A61B 5/0456* | (2006.01) |
| *A61B 5/11* | (2006.01) |
| *G06F 19/00* | (2011.01) |

(52) U.S. Cl.
CPC ........ *A61B 5/1118* (2013.01); *A63B 22/0023* (2013.01); *A63B 22/0235* (2013.01); *A63B 22/0605* (2013.01); *A63B 24/0062* (2013.01); *A63B 24/0075* (2013.01); *A63B 24/0087* (2013.01); *A63B 69/0028* (2013.01); *A63B 71/0686* (2013.01); *G06F 19/3481* (2013.01); *G09B 19/0038* (2013.01); *A63B 22/0076* (2013.01); *A63B 2024/0093* (2013.01); *A63B 2024/0096* (2013.01); *A63B 2071/0625* (2013.01); *A63B 2071/0655* (2013.01); *A63B 2071/0663* (2013.01); *A63B 2220/17* (2013.01); *A63B 2220/30* (2013.01); *A63B 2220/40* (2013.01); *A63B 2220/56* (2013.01); *A63B 2220/805* (2013.01); *A63B 2220/806* (2013.01); *A63B 2220/833* (2013.01); *A63B 2220/836* (2013.01); *A63B 2220/89* (2013.01); *A63B 2225/50* (2013.01); *A63B 2225/54* (2013.01); *A63B 2230/045* (2013.01); *A63B 2230/062* (2013.01); *A63B 2230/207* (2013.01); *A63B 2230/425* (2013.01); *A63B 2230/50* (2013.01); *A63B 2230/60* (2013.01); *A63B 2230/75* (2013.01); *A63B 2244/20* (2013.01)

(58) Field of Classification Search
CPC ............ A63B 24/0075; A63B 24/0087; A63B 69/0028; A63B 71/0686; A63B 22/0076; A63B 2024/0093; A63B 2024/0096; A63B 2071/0625; A63B 2071/0655; A63B 2071/0663; A63B 2220/17; A63B 2220/30; A63B 2220/40; A63B 2220/56; A63B 2220/805; A63B 2220/806; A63B 2220/833; A63B 2220/836; A63B 2220/89; A63B 2225/50; A63B 2225/54; A63B 2230/045; A63B 2230/062; A63B 2230/207; A63B 2230/425; A63B 2230/50; A63B 2230/60; A63B 2230/75; A63B 2244/20; A61B 5/0205; A61B 5/0456; A61B 5/1118; G06F 19/3481; G09B 19/0038

See application file for complete search history.

(56) References Cited

U.S. PATENT DOCUMENTS

| | | |
|---|---|---|
| 4,253,254 A | 3/1981 | Gill |
| 4,541,417 A | 9/1985 | Krikorian |
| 4,867,442 A | 9/1989 | Matthews |
| 5,137,501 A | 8/1992 | Mertsesdorf |
| 5,156,147 A | 10/1992 | Warren |
| 5,423,869 A | 6/1995 | Poore |
| 5,462,504 A | 10/1995 | Trulaske |
| 5,571,075 A | 11/1996 | Bullard |
| 5,697,884 A | 12/1997 | Francischelli |
| 6,132,337 A | 10/2000 | Krupka |
| 6,155,976 A | 12/2000 | Sackner |
| 6,261,236 B1 | 7/2001 | Grimblatov |
| 6,261,250 B1 | 7/2001 | Phillips |
| 6,537,229 B1 | 3/2003 | Wang |
| 6,556,866 B2 | 4/2003 | Dal Molin |
| 6,605,046 B1 | 8/2003 | Del Mar |
| 7,643,873 B2 | 1/2010 | Chan |
| 7,846,104 B2 | 12/2010 | Macquarrie et al. |
| 7,908,013 B2 | 3/2011 | Miesel |
| 8,961,185 B2 | 2/2015 | Bleich et al. |
| 9,457,190 B2 | 10/2016 | Bleich et al. |
| 9,522,317 B2 | 12/2016 | Bleich et al. |
| 2004/0072133 A1 | 4/2004 | Kullok |
| 2004/0077954 A1 | 4/2004 | Oakley |
| 2007/0219059 A1 | 9/2007 | Schwartz et al. |
| 2008/0165017 A1 | 7/2008 | Schwartz |
| 2008/0236369 A1 | 10/2008 | Sasaki |
| 2009/0036938 A1 | 2/2009 | Shipley |
| 2009/0076341 A1 | 3/2009 | James et al. |
| 2010/0189209 A1 | 7/2010 | O'Rouke |
| 2013/0103108 A1 | 4/2013 | Koh et al. |
| 2015/0080746 A1 | 3/2015 | Bleich et al. |
| 2016/0148531 A1 | 5/2016 | Bleich et al. |
| 2017/0014633 A1 | 1/2017 | Bleich et al. |

FOREIGN PATENT DOCUMENTS

| | | |
|---|---|---|
| WO | WO2013028581 | 2/2013 |
| WO | WO2014145863 | 9/2014 |
| WO | WO2016053793 | 4/2016 |
| WO | WO2016085768 | 6/2016 |

OTHER PUBLICATIONS

International Preliminary Report on Patentability and Written Opinion, received in PCT/US2014/030699, mailed Sep. 15, 2015.

Coleman, W., "On the Correlation of the Rate of Beat, Breathing, Bodily Movement Sensory Stimuli", J. Physiol, vol. 54, No. 4, pp. 213-217, Dec. 7, 1920.

Coleman, W., "The Psychological Significance of Bodily Rhythms", The Journal of Comparative Physiology, vol. 1, pp. 213-220, 1921.

Heagerty, A., "Winning rhythm?", The Lancet, vol. 343, pp. 310, Feb. 5, 1994.

Kirby, et al., "Coupling of Cardiac and Locomotor Rhythms", American Physiological Society, 0161-7567/89, pp. 323-329, 1989.

McDonald, D., "Regional Pulse-Wave Velocity in the Arterial Tree", J. Applied Physiology, vol. 24, No. 1, pp. 73-78. 1968.

Murry et al., "Preconditioning with Ischemia: a delay of lethal cell injury in ischemic myocardium", Circulation, vol. 74, No. 5, pp. 1124-1136, 1986.

T. Nakazumi et al., Entrainment of the heart beat into the running pitch during endurance running [I], Japanese J Phys Fitness and Sports Med 1986, vol. 36 No. 6, p. 340.

Nichols et al., "McDonald's Blood Flow in Arteries", Chapter 25 "Exercise", pp. 452-498, Hodder Arnold Publishers, Apr. 28, 2005.

Niizeki et al., "Phase-Dependent Heartbeat Modulation by Muscle Contractions During Dynamic Handgrip in Humans", American Physiolofical Society, 0363-6135/99, pp. H1331-H1338, 1999.

Niizeki K, "Intramuscular pressure-induced inhibition of cardiac contraction: implications for cardiac locomotor synchronization", Am J Physiol Regul Integr Comp Physiol 288: R645-R650, 2005 (First published Nov. 4, 2004; doi:10.1152/ajpregu.00491, 2004).

Nomura, et al., "Analysis entrainment of cardia and locomotor rhythms in humans using the surrogate data technique", European Journal of Applied Physiology, vol. 84, No. 5, pp. 373-378, 2001.

Nomura, et al., "Phase-dependent chronotropic response of the heart during running in humans", Eur J Appl Physiol vol. 97, pp. 240-247, 2006.

(56) References Cited

OTHER PUBLICATIONS

O'Rourke et al., "Improved cardiovascular performance with optimal entrainment between heart rate and step rate during running in human," Coronary Artery Disease vol. 3, pp. 863-869, 1992.

O'Rourke et al., "The rhythm of running: can the heart join in?", Aust NZ J Med, vol. 23, pp. 708-710, 1993.

Palatini et al., "Blood pressure changes during running in humans: the 'beat' phenomenon", American Physiological Society, 0161-7567, 1989.

M. Udo, et al., Entrainment of the heart beat into the running pitch during endurance running [II], Japanese J Phys Fitness and Sports Med 1986, vol. 36, No. 6, p. 341.

D. Zhang, An experimental and modeling study of the relationship between step rate and heart rate during running exercise, Doctorate Thesis, Univerisity of New South Wales, Sidney, Australia, 2002.

Zhang et al., "Possible mechanism for modulating cardiovascular system during running in humans", 23rd Annual International Conference of the IEEE Engineering in Medicine and Biology Society, Oct. 25-26, 2001.

Zhang et al., "Monitoring Physiological Signals during Running Exercise", 23rd Annual International Conference of the IEEE Engineering in Medicine and Biology Society, Oct. 25-26, 2001.

D. Zhang et al., "The effect of heartbeat-synchronised running on the cardiovascular system," Conference Proceedings, 2nd Joint EMBS-BMES Conference 2002, 24th Annual International Conference of the Engineering in Medical and Biology Society, Annual Fall meeting of the Biomedical Engineering Society, IEEE, vol. 2, 2002, pp. 1295-1296.

Zhao et al., "Inhibition of myocardial injury by ischemic postconditioning during reperfusion: comparison with ischemic preconditioning", Am J Physiol Heart Circ Physiol 285: H579-H588, 2003 (first published Apr. 3, 2003; 10,1152/ajpheart.01069, 2002).

International Search Report received in PCT/US2015/052326, mailed Dec. 23, 2015.

International Search Report and Written Opinion received in PCT/US2015/061696, mailed Feb. 2, 2016.

First Exam Report (EPO Form 2906) issued in Application No. 12 754 154.8 dated Jun. 26, 2015.

U.S. Appl. No. 13/589,073, filed Aug. 17, 2012, System and Method for Reliably Coordinating Musculoskeletal and Cardiovascular Hemodynamics.

U.S. Appl. No. 14/553,732, filed Nov. 25, 2014, Systems and Methods for Coordinating Musculoskeletal and Cardiovascular or Cerebrovascular Hemodynamics.

U.S. Appl. No. 14/216,960, filed Mar. 17, 2014, Coordinating Musculoskeletal and Cardiovascular Hemodynamics.

U.S. Appl. No. 15/278,617, filed Sep. 28, 2016, Coordinating Musculoskeletal and Cardiovascular Hemodynamics.

U.S. Appl. No. 14/553,725, filed Nov. 25, 2014, Systems and Methods for Coordinating Musculoskeletal and Cardiovascular or Cerebrovascular or Hemodynamics.

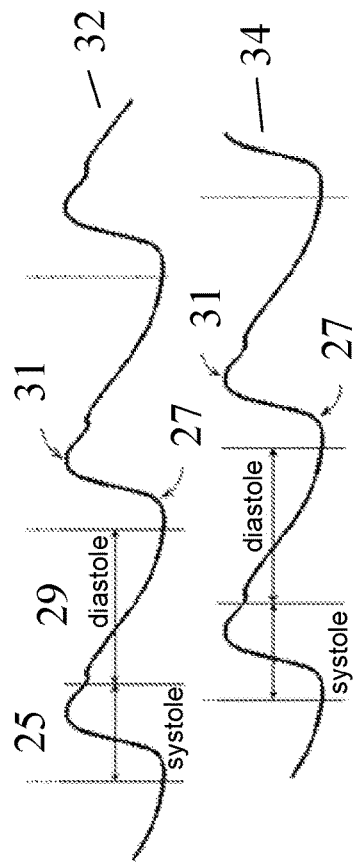
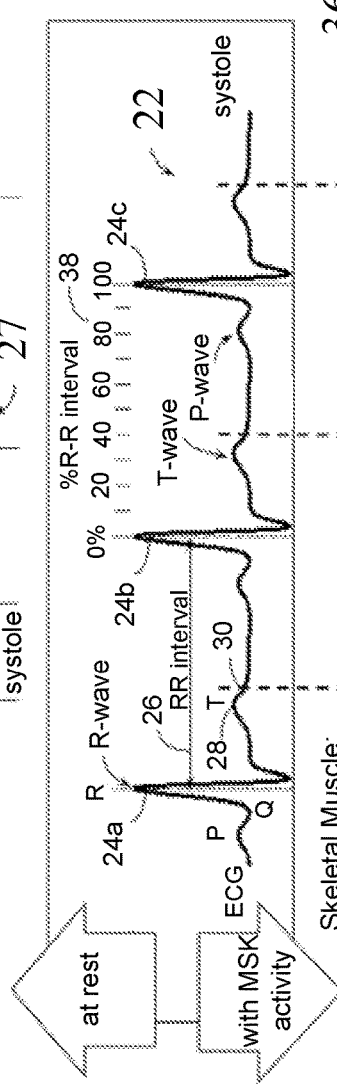
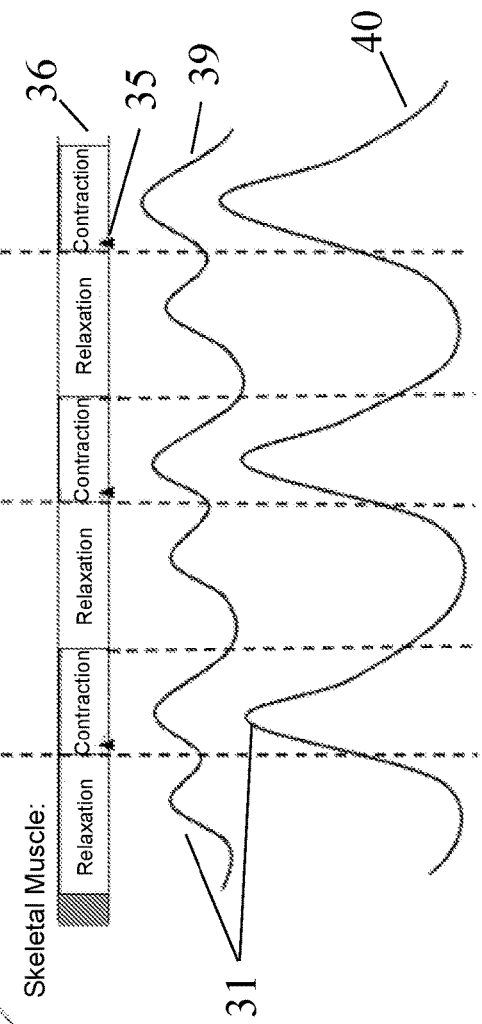
Figure 4A
Figure 4B
Figure 4C

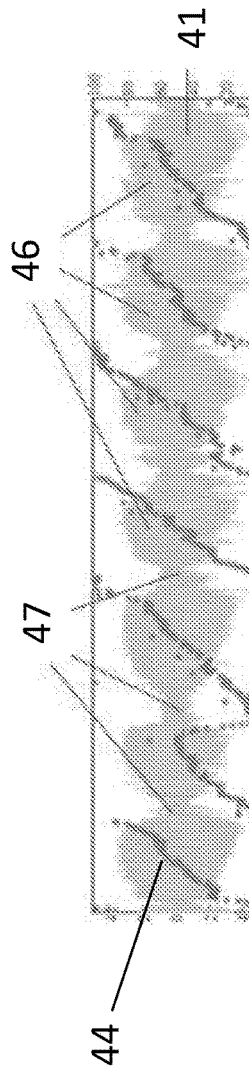
Figure 6A
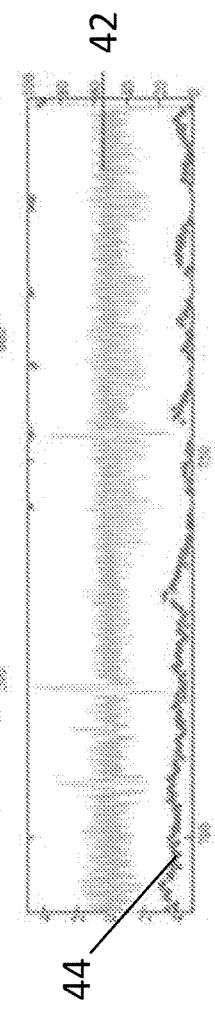
Figure 6B
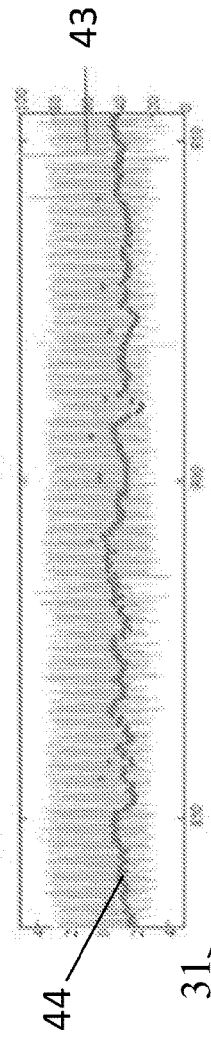
Figure 6C
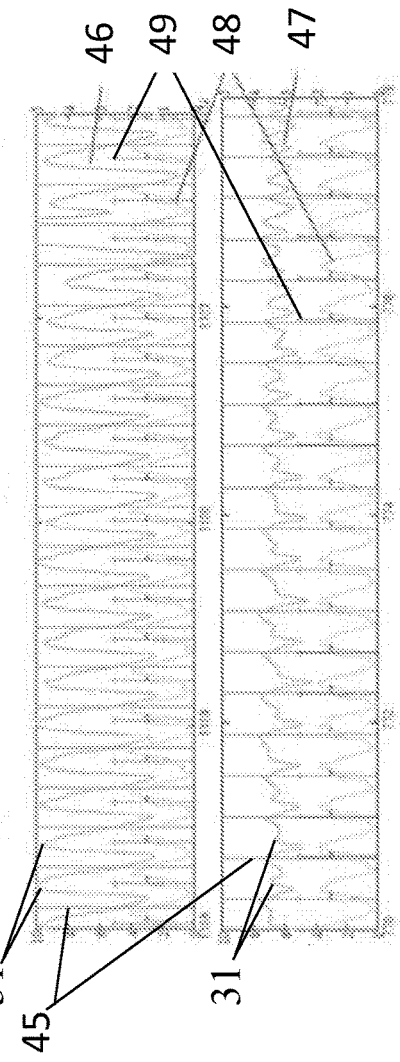
Figure 6D
Figure 6E

SYSTEMS AND METHODS FOR COORDINATING MUSCULOSKELETAL AND CARDIOVASCULAR OR CEREBROVASCULAR HEMODYNAMICS

CROSS-REFERENCE TO RELATED APPLICATIONS

This application is a continuation of U.S. patent application Ser. No. 14/553,732, titled "Systems and Methods for Coordinating Musculoskeletal and Cardiovascular or Cerebrovascular Hemodynamics", filed Nov. 25, 2014, which is a continuation-in-part to co-pending U.S. patent application Ser. No. 13/589,073, titled "System and Method for Reliably Coordinating Musculoskeletal and Cardiovascular Hemodynamics", filed on Aug. 17, 2012, and which claims priority to U.S. provisional patent application Ser. No. 61/525,689, titled "System and Method for Selectively Coordinating User Movement and Muscle Contraction with User Cardiac Pumping Cycle", filed on Aug. 19, 2011, each of which is herein incorporated by reference in its entirety. This application is also related to U.S. patent application Ser. No. 14/216,960, titled "Coordinating Musculoskeletal and Cardiovascular Hemodynamics", filed on Mar. 17, 2014, which claims priority to U.S. provisional patent application Ser. No. 61/798,799, titled "Systems and Methods for Reliably Coordinating Musculoskeletal and Cardiovascular Hemodynamics", filed on Mar. 15, 2013, both of which are herein incorporated by reference in their entirety. This application is related to U.S. provisional patent application Ser. No. 62/056,730, titled "Coordinating Musculoskeletal and Cardiovascular Hemodynamics", filed on Sep. 29, 2014, which is herein incorporated by reference in its entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

This invention relates generally to the field of human physiology, and more specifically to new and useful methods, apparatuses, systems and computer program products for coordinating musculoskeletal and cardiovascular or cerebrovascular hemodynamics.

BACKGROUND

Blood is circulated through the body by the heart during its rhythmic pumping cycle, which consists of two distinct periods—systole and diastole. Heart muscle contracts to eject blood from the ventricles during the systolic period of each cardiac cycle (CC). Ejection of blood from the ventricles generates arterial blood pressure and flow adequate to deliver blood throughout the body. The blood transports oxygen, nutrients and metabolic products, removes carbon dioxide and waste, and facilitates critical physiological functions such as heat exchange. The heart subsequently relaxes during the diastolic period of the CC, when the atrial and ventricular chambers refill with blood in preparation for the heart's next contraction.

Unlike the rest of the body, which receives most of its blood flow during the systolic portion of the arterial pressure cycle, contraction of the heart during systole generates high forces within the heart's muscular walls, preventing blood from flowing through the heart muscle itself at that time. Therefore, the heart's own arterial blood supply is delivered primarily during diastole, when the heart muscle is relaxing and the heart chambers are filling for the next contraction, while at the same time the lower residual blood pressure in the aorta pushes blood through the coronary arteries and into the myocardial muscle to supply the heart with its needed oxygen and nutrients.

In addition to the heart's pumping function, the musculoskeletal (MSK) system also pumps arterial and venous blood throughout the body during physical activity in a couple of important ways. First, skeletal muscle contraction and relaxation cycles during rhythmic physical activities cause regular oscillations in peripheral arterial and venous blood pressure or flow due to intermittent compression of the vasculature that travels within, between, and adjacent to the skeletal muscles. Second, MSK movement can lead to periodic acceleration and deceleration of the intravascular volume of blood against gravity and inertia.

When rhythmic muscle contractions and MSK movements are favorably coordinated with the timing of the heart's pump cycle, the MSK and cardiac pumping systems can augment one another to increase blood flow to and perfusion of important areas of the body with less pumping energy expended by the heart. This favorable coordination of these two pumping systems can be referred to as "musculoskeletal counterpulsation" (MCP). During MCP, maximum rhythmic MSK-induced blood pumping consistently increases central arterial blood pressure when the heart is relaxing and refilling between contractions (i.e. during diastole), and the maximum cardiac induced pumping (systole) consistently occurs between MSK induced maximal central arterial pressure events. On the other hand, when rhythmic muscle contractions and MSK movements occur with uncoordinated, or worse, unfavorably coordinated timing, blood flow and perfusion are decreased along with a concurrent decrease in pumping efficiencies. Unfavorable coordination occurs, for example, when the cardiac and MSK systems consistently pump blood maximally into the central circulation at substantially the same time during rhythmic physical activity. This unfavorable coordination of the two pumping systems can be referred to as "inverse musculoskeletal counterpulsation" (iMCP).

Typically, when individuals walk, run, bicycle, or participate in any rhythmic physical activity, most experience favorable coordination between MSK blood pumping and CC blood pumping only intermittently. Even when an individual's heart rate (HR) and MSK activity cycle rate (MSKR) happen to be substantially equal, the respective timing of the two pumping systems may result in favorable or unfavorable coordination, or somewhere in between. A certain degree of "cardio-locomotor synchronization" can occur during rhythmic physical activity, in which the timing of an individual's MSK pump cycle relative to the heart's pump cycle tends, statistically, to naturally favor MCP.

However, when such synchrony does occur, it is usually only a temporary phenomenon since HR and/or MSKR can change as environmental factors vary (e.g., running in hilly terrain or variable wind) or with any of several physical changes, such as alterations in effort, speed, hydration, temperature, catecholamine levels, or fatigue.

The benefits of favorable coordination between MSK movements and the heart's pump cycle can include improved perfusion and oxygenation of cardiac and peripheral skeletal muscle and possibly other tissues; decreased HR due to increased cardiac preload and stroke volume; decreased systolic blood pressure and pulse pressure; decreased required respiratory effort to meet decreased oxygen demands; and reduced muscle fatigue due to improved skeletal muscle perfusion. These benefits can potentially lead to increased physiological efficiency, decreased myocardial stress, increased aerobic energy production, improved aerobic fat metabolism, enhanced individual performance, and a potential increase in the health benefits and safety of rhythmic physical activity. Conversely, unfavorable coordination between MSK movements and the heart's pump cycle can lead to the opposite of all of these effects.

Some of the general approaches that we have described for favorably coordinating MSKC and CC timing during rhythmic physical activity include (1) the provision of adaptive real-time MSKC timing prompts to a user, (2) automated means of adjusting exercise equipment settings in order to adaptively modify a user's MSKC timing; and (3) automated means of adjusting artificial cardiac pacemaker systems to adaptively adjust the timing of the CC relative to the MSKC of the user. Each of these general approaches may require the identification and use of sensed physiological metrics to assist with identifying a target timing relationship between the MSKC and CC of the user, measuring physiological impacts of the timing relationship, and tracking progress in favorably influencing physiology over time.

The methods and systems described below are for guiding a user to obtain and maintain favorable coordination of MSKC and CC hemodynamics, and more directly, to achieve or maintain system calibration, to increase the accuracy of identifying, achieving, and maintaining target pump timing relationships, and/or to track the effectiveness of achieving physiological benefit during rhythmic physical activity.

SUMMARY

Described herein are methods for guiding a user to a target rhythmic musculoskeletal cycle activity (MSKC) to cardiac cycle (CC) timing relationship. In general, the methods may include detecting a first signal responsive to the timing of the CC of a user using a first sensor; determining the heart rate (HR) of the user using at least a portion of the first signal detected by the first sensor using a first processor, providing a recurrent prompt from a prompt device to the user as a timing indication for performance of a rhythmic musculoskeletal activity; detecting a second signal responsive to the rhythmic musculoskeletal activity timing of the user that repeats at an MSKR of the user using a second sensor; determining an actual MSKC to CC timing relationship between the first signal and the second signal using the first processor, comparing the actual timing relationship of the first signal and the second signal to a target MSKC to CC timing relationship; and adjusting the timing indication of the recurrent prompt from the prompt device to the user based on a difference between the actual timing relationship and the target timing relationship, so as to reduce the magnitude of the difference.

In some embodiments, the target timing relationship is provided by the first processor or a second processor. In some embodiments, the timing indication guides the user to a musculoskeletal activity cycle rate (MSKR). In some embodiments, the HR of the user is substantially an integer multiple of the MSKR. In some embodiments, the recurrent prompt repeats at a prompt rate such that the HR is substantially an integer multiple of said prompt rate. In some embodiments, adjusting the timing indication of the recurrent prompt from the prompt device includes adjusting the prompt rate. In some embodiments, the recurrent prompt is an audible prompt that includes a beat of a musical track. In some embodiments, a volume of the beat of the musical track that includes the recurrent prompt is controlled separately from a volume of a rest of the musical track based on a user setup configuration, a program setup configuration, a consistency of the user in stepping to the recurrent prompt, and/or an accuracy of the user stepping at the timing indication. In some embodiments, the first sensor signal includes at least one of an electrocardiogram (ECG) and a plethysmogram. In some embodiments, the second sensor includes an accelerometer, an electromyographic sensor, a pressure sensor, a switch, a camera, a gryroscope, a proximity sensor, and/or a plethysmographic sensor.

In some embodiments, detecting the first signal includes identifying instances of one or more features of the first signal that occur once per CC. In some embodiments, the features correspond to one or more of an ECG R-wave, an ECG T-wave, an end of the ECG T-wave, a peak of a cardiovascular systolic pressure, a nadir of a diastolic cardiovascular pressure, and a transition point in a cardiovascular pressure of the user. In some embodiments, the method further includes determining the MSKR of the user, using the first processor or the second processor, based on the second signal detected by the second sensor.

Described herein are methods for determining a target MSKC to CC timing relationship. In general, the methods may include detecting a first characteristic of a signal responsive to a CC timing of a user that repeats at a frequency that corresponds to a HR of the user using a first sensor, detecting a second characteristic of a signal responsive to a rhythmic MSKC timing of the user that repeats at a frequency that corresponds to the MSKR of the user using the first sensor or a second sensor; determining a value representative of an actual timing relationship between the first characteristic and the second characteristic using a first processor, detecting a third characteristic of a signal using the first, the second, or a third sensor corresponding to a physiological metric that varies with the actual timing relationship between the first and second characteristics; and determining a target value representative of a preferred timing relationship between the first and second characteristics by identifying the value representative of the actual timing relationship that corresponds with a preferred value of the variable physiological metric, using the first processor or a second processor.

In some embodiments, the method further includes providing a recurrent prompt from a prompt device at a prompt rate to the user as a timing indication for performance of the rhythmic MSKC. In some embodiments, the prompt device is controlled by the first processor or the second processor. Further, in some embodiments, the HR of the user is substantially an integer multiple of the prompt rate. In some embodiments, the prompt rate is provided to guide the user to vary the MSKC timing relative to the CC timing. In some embodiments, the target value representative of the preferred timing relationship is naturally achieved by the user. In some embodiments, the prompt device prompts the user to maintain the naturally achieved preferred timing relationship. In some embodiments, the prompt device is configured by the first or second processor to controllably guide the user to at least two different actual timing relationships. In some embodiments, at least two of the first, second, or third characteristics are aspects of a first signal from the first sensor. In some embodiments, the at least one of the first, second or third characteristics includes a Fourier transform. In some embodiments, the value representative of an actual timing relationship is determined by using a cross correlation between the first characteristic from the first sensor and the second characteristic from the second sensor. In some embodiments, the first characteristic and the second characteristic are derived from independent first and second signals from the first and second sensors, respectively. In some embodiments, the physiological metric includes the HR, a tissue pH, a tissue lactic acid level, a respiratory volume, a respiratory exchange ratio, an oxygen consumption, or a $CO_2$ production of the user.

In some embodiments, the method further includes prompting an adjustment of the cadence of the user to guide the user towards the target relative timing relationship. In some embodiments, the method further includes guiding the user to the HR and a MSKR, such that an absolute difference between the two rates is between 0.25 and 5 per minute. In some embodiments, the preferred value of the variable physiological metric is a most commonly occurring actual timing relationship. In some embodiments, the user achieves the target timing relationship without prompting when the HR and the MSKR are approximately equal. In some embodiments, the preferred value of the variable physiological metric is a most commonly occurring actual timing relationship. In some embodiments, the first sensor technology includes photoplethysmography, impedance plethysmography, laser-Doppler blood flow, acoustic sensing, or arterial tonometry. In some embodiments, the preferred value of the physiological metric is a lowest average HR of the user.

Described herein are methods for favorably coordinating a timing relationship between an MSKC of a rhythmic musculoskeletal activity of a user and a CC of the user. In general, the methods may include repetitively detecting a signal responsive to cyclically-varying arterial blood volume in a tissue of the user, using a sensor; determining a first measured characteristic of the signal that repeats at a HR of the user and determining the HR of the user from the first characteristic; recurrently providing a guidance prompt from a prompt device to the user as a timing indication for performance of a rhythmic MSK activity, determining a value of a second measured characteristic of the signal that varies with an actual MSKC to CC timing relationship of the user; and adjusting the guidance based on a trend of the value of the second measured characteristic towards a relative preferred value of the second measured characteristic corresponding to a target MSKC to CC timing relationship, thereby guiding the user towards substantially obtaining and maintaining the target MSKC to CC timing relationship. In some embodiments, the HR is an integer multiple of the rate of the timing indication.

Described herein are methods for favorably coordinating a timing relationship between an MSKC of a rhythmic musculoskeletal activity of a user and a CC of the user. In general, the methods may include recurrently providing a movement guidance from a prompt device to the user for guiding performance of a rhythmic musculoskeletal activity; and, repetitively, detecting a signal, using a sensor, that correlates to a cyclically-varying arterial blood volume in a tissue of the user; determining an actual value of a measured characteristic of the signal that varies with the timing relationship between the MSKC and the CC of the user, using a processor, and computing a trend of the actual value of the measured characteristic using a processor, and adjusting the movement guidance based on the trend of the actual value so as to cause the actual value of the measured characteristic to approach a relative preferred value of the measured characteristic.

In some embodiments, the movement guidance includes at least one of a recurrent audible, visual, or tactile prompt. In some embodiments, the detecting step includes using as the sensor technology photoplethysmography, impedance plethysmography, laser-Doppler blood flow, acoustic sensing, or arterial tonometry. In some embodiments, the measured characteristic of the signal that varies with the timing relationship between the MSKC and the CC of the user includes at least one of a pulse amplitude, a measure of relative peak to valley signal waveform curvature, a measure of signal waveform peak curvature, a measure of signal waveform valley curvature, a measure of signal waveform complexity, and a measure of an asymmetry of the signal waveform. In some embodiments, the relative preferred value of the measured characteristic is a threshold crossing of an increasing trend, a threshold crossing of a decreasing trend, a local maximum, or a local minimum of the trend of the actual value of the measured characteristic. In some embodiments, a heart rate of the user is substantially an integer multiple of the prompt rate.

In some embodiments, the method further includes detecting, using one or more sensors, signals that correlate to a heart rate of the user and a musculoskeletal activity cycle rate (MSKR) of the user; determining, using the processor, the heart rate of the user and an MSKR of the user by processing the one or more signals; specifying a maximum allowable absolute difference between the heart rate and the MSKR; and executing, using the processor, the above-mentioned steps of: recurrently providing a movement guidance from a prompt device to the user for guiding performance of a rhythmic musculoskeletal activity; and, repetitively, detecting a signal, using a sensor, that correlates to a cyclically-varying arterial blood volume in a tissue of the user, determining an actual value of a measured characteristic of the signal that varies with the timing relationship between the MSKC and the CC of the user, using a processor, and computing a trend of the actual value of the measured characteristic using a processor; and adjusting the movement guidance based on the trend of the actual value so as to cause the actual value of the measured characteristic to approach a relative preferred value of the measured chaiacteristic, only when an absolute value of a difference between the MSKR and heart rate is less than, or less than or equal to, a specified allowable difference.

In some embodiments, the method further includes specifying a target MSKR; and recurrently providing a prompt from the prompt device when the absolute value of the difference between the MSKR and the target MSKR is greater, or greater than or equal to, the specified allowable difference, the prompt repeating at a prompt rate.

In some embodiments, the target MSKR is an integer multiple of the prompt rate. In some embodiments, the measured characteristic of the signal is computed using a combination of two or more unique characteristics of the signal that vary with the timing relationship between the MSKC and the CC of the user. In some embodiments, the method further includes detecting with the sensor a second signal that correlates to the HR or the MSKR of the user. In some embodiments, the method further includes detecting with a second sensor signals that correlate to the HR or the MSKR of the user. In some embodiments, the target cadence equals a target heart rate of the user. In some embodiments, the movement guidance includes instructing the user in at least one of an MSK activity timing and an MSK activity effort. In some embodiments, instructing the user in the MSK activity effort includes providing movement guidance on stride length during running or walking, gear use while riding a bicycle, resistance, MSKC movement distance, incline using exercise equipment, or stroke length during rowing or swimming. In some embodiments, instructing the user in the MSK activity timing includes providing an MSKC prompt at a prompt rate to guide the user to an MSKR that is an integer multiple of the prompt rate.

In some embodiments, the method further includes a calibration process, said calibration process including detecting a second characteristic of at least one of the signal and one or more additional signals corresponding to a physiological metric that varies with the timing relationship between the MSKC and the CC of the user, using the sensor or one or more additional sensors; and determining the relative preferred value of the measured characteristic as a relative value of the trend that corresponds with a preferred value of the physiological metric.

In some embodiments, the physiological metric includes a measure of heart rate, minute ventilation, blood pressure, blood flow, cardiac output, electrical brain activity, oxygen consumption, tissue pH, tissue lactic acid level, or CO2 production. In some embodiments, the relative preferred value is a target behavior of the trend of the value of the measured characteristic and includes further adjusting the guidance based on a difference between trend of the actual value of the measured characteristic and the relative preferred value of the measured characteristic. In some embodiments, the recurrent guidance guides the user towards substantially obtaining and maintaining the relative preferred value of the measured characteristic.

In some embodiments, the relative preferred value is a target value of the measured characteristic including further adjusting the guidance based on a difference between the actual value of the measured characteristic and the relative preferred value of the measured characteristic. In some embodiments, the target value corresponds to the target timing relationship between the MSKC and the CC of the user. In some embodiments, the recurrent guidance guides the user towards substantially obtaining and maintaining the relative preferred value of the measured characteristic.

Described herein are systems for favorably coordinating a timing relationship between an MSKC of a rhythmic musculoskeletal activity of a user with a CC of the user. In general, the system may include a prompt device, such that the prompt device is configured to provide recurrently a movement guidance to the user for guiding performance of the rhythmic musculoskeletal activity. In general, the system may include a sensor, such that the sensor is configured to provide a signal that correlates to a cyclically-varying arterial blood volume in a tissue of the user. In general, the system may include a processor, coupled to the prompt device and the sensor, such that the processor is configured to determine an actual value of a measured characteristic of the signal that varies with the timing relationship between the MSKC and the CC of the user, and further configured to adjust the movement guidance based on the trend of the actual value so as to cause the actual value of the measured characteristic to approach a relative preferred value of the measured characteristic.

In some embodiments, the measured characteristic of the signal that varies with the timing relationship between the MSKC and the CC of the user includes at least one of a pulse amplitude, a peak to valley measure of signal waveform curvature, a measure of signal waveform peak curvature, a measure of signal waveform valley curvature, a measure of signal waveform complexity, and a measure of an asymmetry of the signal waveform. In some embodiments, the relative preferred value of the measured characteristic is a threshold crossing of an increasing trend, a threshold crossing of a decreasing trend, a local maximum, or a local minimum of the trend of the actual value of the measured characteristic. In some embodiments, the sensor technology includes photoplethysmography, impedance plethysmography, laser-Doppler blood flow, acoustic sensing, or arterial tonometry.

BRIEF DESCRIPTION OF THE DRAWINGS

FIGS. 4A-C illustrate a timing relationship between central arterial pressure waveforms, peripheral arterial pressure waveforms, an electrocardiogram tracing, a targeted rhythmic musculoskeletal contraction cycle, and a timing of sensed MSKC events of a user, in accordance with preferred embodiments;

FIGS. 6A-G illustrates a series of photoplethysmography, ECG, and accelerometer signals of a user, in accordance with preferred embodiments;

DETAILED DESCRIPTION

Figure 1:
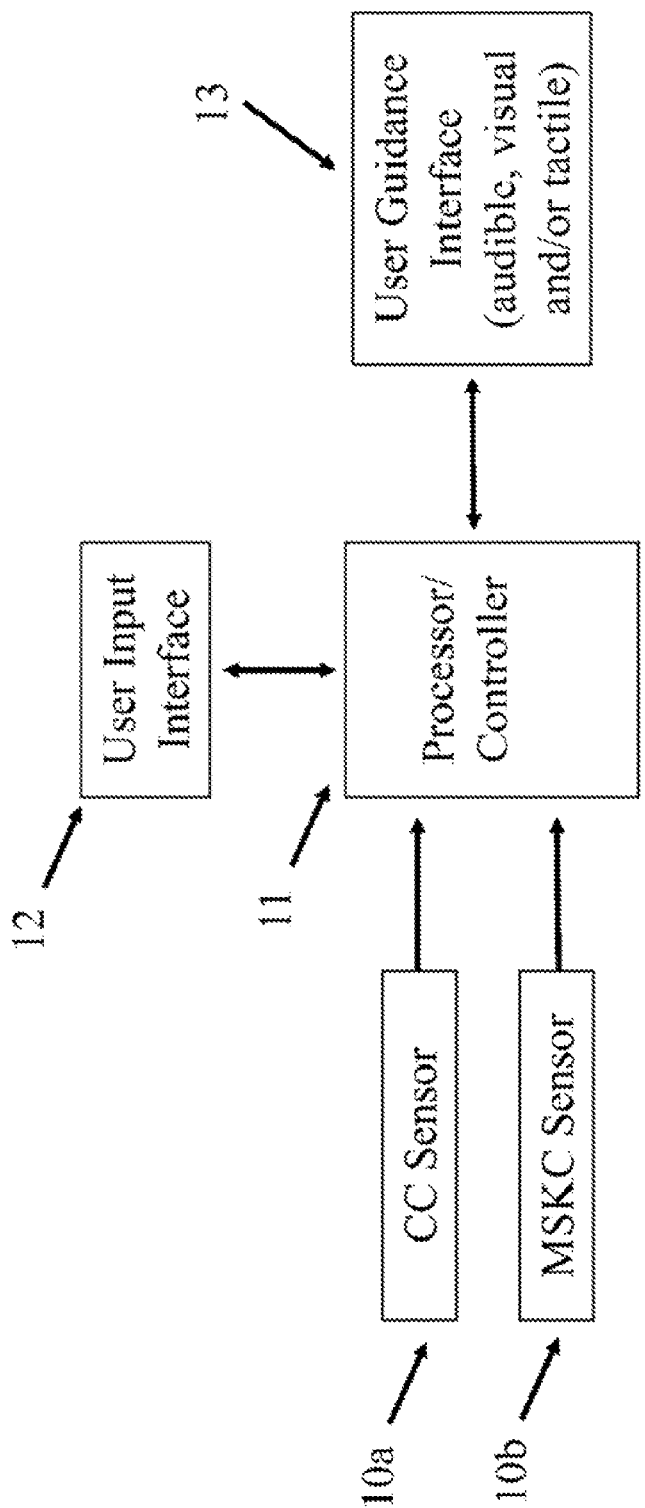
FIG. 1 illustrates a system for determining a target MSKC to CC timing relationship and guiding a user to the target MSKC to CC timing relationship, in accordance with a preferred embodiment.

The following description of the preferred embodiments of the invention is not intended to limit the invention to these preferred embodiments, but rather to enable any person skilled in the art to make and use this invention. Disclosed herein are systems and methods for favorably coordinating musculoskeletal and cardiovascular or cerebrovascular hemodynamics.

In this disclosure, the terms cardiac cycle ("CC"), cardiovascular cycle, and cardiac pump cycle may be considered synonymous, referring to the activity of the heart during a single, complete, heart pump cycle (equivalently, a single heartbeat). The terms heart rate ("HR"), cardiac or cardiovascular cycle rate, and cardiac pump cycle rate may be considered synonymous. Numerous key aspects of the cardiac pumping cycle, as well as detectable signals that reflect those aspects, occur only once per heartbeat. These include, for example, elements of the heart's electrical activity, corresponding periods of cardiac muscle contraction (systole) and relaxation (diastole), the filling and emptying of the chambers of the heart, the individual heart valves opening and closing, and the associated arterial blood pressures and flows. Each of these aspects, elements, components, or events reoccurs with every heartbeat. Further, the phrases blood pressure, pressure, or arterial pressure may be used interchangeably, as when describing sensors, waveforms, or signals responsive to at least one of arterial blood pressure, volume, or flow, such as a plethysmographic sensor, for example.

In this disclosure, the terms musculoskeletal activity cycle and musculoskeletal activity pump cycle may be considered synonymous. As disclosed herein, MSKC equivalently may refer to the activity of the MSK during a single, complete, MSK pump cycle (e.g. a single stride or step running, pedal push biking [½ revolution of the pedal], stroke swimming, or pull rowing). Numerous key aspects of the MSKC, as well as detectable signals that reflect those aspects, occur only once per MSKC. One MSKC refers to the activity of the MSK system that results in peripheral vascular blood pumping during a single cycle of the rhythmic physical activity of the user. Musculoskeletal activity rate ("MSKR"), musculoskeletal activity pump cycle rate, musculoskeletal pump rate, and cadence may be considered synonymous, not to be confused with the fact that the term cadence can alternatively be commonly used to reference a multiple of the true MSKR (e.g. bicycle RPM ["cadence"] of 90→MSKR of 180, because there are two MSK pumping activities, one per leg, for each full revolution of the bicycle pedals). Examples of common MSKRs during physical activity include stride frequency in walking or running, leg pumping rate while pedaling on a bicycle, stroke rate when swimming or rowing, etc. Further, different MSKCs may occur simultaneously in a single user at different rates. For example, a swimmer may kick with their legs at a multiple of the rate that they pull with their arms and each of a rower's strokes includes both a pull and a push of the oars. In the following disclosure, the terms synchronize and coordinate, and derivatives of these terms, may be used synonymously to describe any type of consistently repeated pump timing relationship.

Described herein are systems and methods for coordinating CC and MSKC pumping activities to achieve MCP. MCP is considered optimized for a rhythmic physical activity when the CC and the MSKC are synchronized (i.e., coordinated) in a complimentary fashion such that the MSKC pumps maximal blood cumulatively into the central circulation (e.g. aorta) during early CC diastole, and the heart pumps blood maximally into the central circulation at the most overall favorable relative timing to the MSKC. As used herein, this optimal relative timing of the CC and MSKC pumps is generally considered the target MSKC to CC timing relationship. CC and MSKC pumping activities are coordinated to achieve MCP by guiding a user to a target MSKC to CC timing relationship, and MCP is achieved when a user attains the target MSKC to CC timing relationship. In some embodiments, a user is guided to achieve MCP. Alternatively, in certain other embodiments, a user is guided to avoid inverse MCP (iMCP) in which the two pumping systems are coordinated unfavorably. The systems and methods described herein may take into account that, in some instances, a user may achieve MCP naturally during rhythmic MSK activity, at least for a period of time, without any external input.

Rhythmic MSK activity as described herein may refer to biking, running, rowing, walking, swimming, and/or any other type of rhythmic activity. Rhythmic may refer to any repeating pattern (e.g. 1, 2, 1, 2 . . . ; or 1, 2, 1, 2, 3, 1, 2, 1, 2, 3 . . . ). For example, during running, the rhythmic stepping pattern may comprise: left foot, right foot, left foot, right foot, etc., where the steps occur with every heartbeat or with every other heartbeat. Alternatively, during rowing, rhythmic may comprise each stroke of the paddle in the water, where the stroke is timed based on the heartbeat, but not each heartbeat or necessarily using the same number of heartbeats between each stroke. Additionally, different parts of the MSK system of a user may simultaneously maintain different rhythms, e.g. during certain swimming strokes, a lower extremity kick rate may occur at a higher frequency than an upper extremity stroke rate.

In some embodiments, the system monitors a MSKC to CC timing relationship of the user and prompts, motivates, or otherwise guides the user to reach a target MSKC to CC timing relationship and thereby achieve MCP. A user of the system described herein may be any person performing rhythmic musculoskeletal activity. Peripheral or central physical locations adjacent to the circulation of a user, for example, locations on the arm, wrist or finger of an upper extremity, the ear lobe or canal, forehead, temple, retina, or elsewhere on the head may be monitored to determine a timing relationship from sensed hemodynamic effects (e.g. changes in arterial blood flow, volume, or pressure). As described herein, the timing relationship may be the timing relationship between the MSKC timing and the CC timing. In some embodiments, the timing relationship may be described as a phase relationship of the CC and MSKC pumping activities or the signals responsive to the respective pumping activities, or a time offset between them.

In further embodiments, a target HR may be chosen prior to or during an activity, based, for example, on comfort, preferred MSKR, desired effort, type of run (e.g. intervals, speed, etc.), coached target, calibration run, or a calculation based on calculated and tested or entered maximum HR.

In some embodiments, a MSKC to CC timing relationship of a user may be monitored and/or guided using an application on an electronic device, for example a mobile phone or a laptop. The application may run constantly in the background, for example, in a head mounted "smartglass" heads-up display/processor, an ear mounted "smart headphone" or earbud audio/processor, or in a wrist mounted "smartwatch" display/processor. The application may offer a prompt, such as an icon or audible signal that conveys that the HR is substantially an integer multiple of the MSKR, e.g. "HR≈step rate" during running or "HR≈2×step rate" during hiking up an incline. In some ambulation embodiments, the application may query the user whether or not the user would like to step to the beat. In accordance with preferred embodiments described herein, prompting a user to move to the beat may only occur when the HR and the MSKR of the user are naturally substantially aligned, for example, when the user's HR equals approximately an integer multiple of the frequency of his or her MSK activity.

In some embodiments, information about a user may be tracked, using appropriate sensors, before, during, and/or after one or more MSK activities. This information may be used during calibration of a target MSKC to CC timing relationship, for guiding the user to the target MSKC to CC timing relationship, and for tracking a user's progress toward the target MSKC to CC timing relationship during use of the system. For example, subjective information may be tracked, such as a difficulty, satiety, energy level, or satisfaction "index." The index may rely on feelings and/or emotions of the user regarding the exercise experience and how the body feels at periods before, during, and/or after the MSK activity. Other subjective information may be used, including pleasure and pain. Further, information including the amount of weight loss or gain that the user experiences may be tracked. For example, the system may enable a user to record his or her weight at a certain point before, during, and/or after the MSK activity. Weight data may be correlated with other measurements to provide useful information to the user.

In some embodiments, respiratory information is tracked. Such information includes, for example, respiratory exchange ratio, minute volume (VE), volume of $CO_2$ produced, volume of $O_2$ consumed, $O_2$ debt, and/or force of expiration. By tracking the user's respiratory information, and by presenting trends or changes in the respiratory information, the energy conservation advantage of the system is readily communicated to the user.

Other trackable information for calibrating, guiding, and measuring progress during use of embodiments of the system may relate to skin, muscle, interstitial fluid, and blood characteristics. For example, monitoring continuous or intermittent glucose or insulin levels may be useful, particularly for persons with diabetes. Alternatively or additionally, lactic acid or pH levels may also be tracked. In some embodiments, retinal, facial, muscular, and/or cerebral blood flow may be sensed and tracked. Retinal pulse embodiments may be captured, for example, by cameras. Pupil reactions may also be monitored. Acute, chronic, central, and peripheral blood pressure may also be tracked. Stroke volume and cardiac output may be tracked. Examples of capturing brain function and perfusion may extend beyond cerebral blood flow, to include EEG (electroencephalogram) sensed from a head mounted system or measures of cognitive function. HR variability may be measured to enable tracking of stress levels or other general health and fitness information. Further, information may be tracked that relates to the intensity, duration, ergonomics, and effectiveness of an activity, such as movement, acceleration, speed, magnitude of muscle contraction, and/or force per second. Sensed signals might include, for example, electromyography (EMG), accelerometry, pressure sensors, etc.

Other types of metrics may be measured, recorded, and/or used by the system during physical activity. In some embodiments, metrics may include efficiency metrics. Exemplary physical activity related efficiency metrics may include watts/beat (e.g. power per heart beat while pedaling a bicycle); watts/HR; [Δdistance×Δelevation]/beat; Δdistance/Δelevation/HR; and [gradient×distance]/HR. Slope, tilt or inclination can be expressed in a variety of ways, including, but not limited to 1) a ratio of the rise to the run, for example 1/20; 2) an angle, for example in degrees; and 3) a percentage called the "grade" (rise/run×100). Further exemplary metrics may include a "pulse-pace", such as [heart beats]/mile; miles/beat; ft/beat, km/beat, watts/beat, strokes-mile, or rpm/mile may be monitored and tracked (wherein "beat"=heart beat).

Systems

Figure 2:
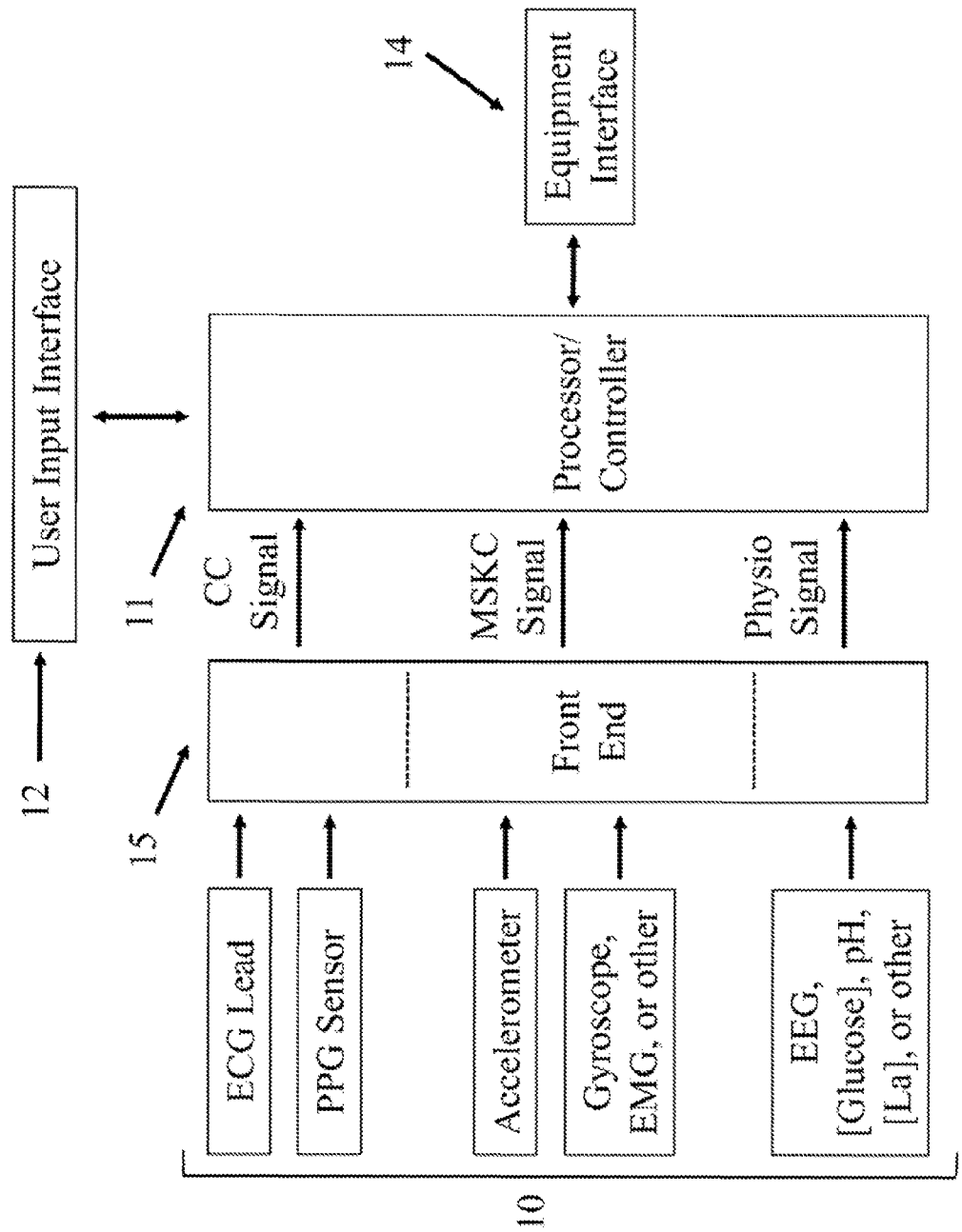
FIG. 2 illustrates a system for receiving cardiac, musculoskeletal, or physiological cycle signals to determine a target MSKC to CC timing relationship and to guide the user to the target MSKC to CC timing relationship, in accordance with an alternative preferred embodiment.

FIGS. 1 and 2 illustrate a system for determining a target MSKC to CC timing relationship and guiding a user to the target MSKC to CC timing relationship, in accordance with a preferred embodiment. The system as shown in FIGS. 1 and 2 may be combined into one device or maintained as two or more separate devices in communication with one another. The system may be placed on or mounted to exercise or gaming equipment used or worn by a user. A wearable system may include a chest strap, helmet, headband, hat, visor, sports bra, shoe, watch, wristband, armband, ankle bracelet, headset, earpiece, earbuds, glasses/goggles, contact lens, embedded chip, patch, and/or any other type of adhesive, wearable, or mountable device. Equipment may include a bike, treadmill, elliptical trainer, stair stepper, rowing machine, boat, paddle, pacemaker, video gaming system, powered exoskeleton bionic devices, and/or any other type of equipment used during rhythmic physical activity. Use and manipulation of exercise equipment to determine a target MSKC to CC timing relationship of a user and to guide a user towards the target MSKC to CC timing relationship will be discussed in further detail below in connection with FIGS. 8 and 9.

As shown in FIGS. 1 and 2, a system for determining a target MSKC to CC timing relationship includes one or more sensors, detectors, or sensing elements 10a, 10b (collectively 10) for delivering or transmitting information to one or more processors/controllers 11. The processor 11, as shown in FIGS. 1 and 2, processes, converts, or otherwise transforms the sensor information using hardware and software and transmits or delivers the resulting relevant guidance and/or adjustment information to at least one of a user input interface 12, user guidance interface 13, or an equipment interface 14. Optionally, the system may include a front end 15, as shown in FIG. 2. The front end 15 preprocesses, transforms, separates, or otherwise deciphers information received from the one or more sensors 10 and transmits the information to the processor 11. In some embodiments, transmitting, delivering, or otherwise transferring information between system components may be accomplished wirelessly (e.g. through cellular, Wi-Fi, Bluetooth, ultrasound, or ANT+ technologies), and/or through a hardwired connection. For example, the hardwired connection may include an electrical connection, universal serial bus (USB), or FireWire, for example Apple's IEEE 1394 High Speed Serial Bus.

In some embodiments, as shown in FIGS. 1 and 2, a sensor, detector, or sensing element 10 is used to detect a physiological parameter, feature, or metric and transmit the information about the physical parameter in the form of a raw or pre-processed signal. A sensor technology 10 may, for example, include electrocardiography (ECG), accelerometry, electromyography (EMG), electroencephalography (EEG), plethysmography (e.g., photoplethysmography (PPG) or impedance plethysmography (IPG)), arterial tonometry, or use of a pressure sensor, a switch, a camera, a gryroscope, a proximity sensor, a glucose sensor, a pH sensor, a lactic acid sensor, laser-Doppler blood flow, and/or an acoustic sensor (e.g. ultrasound, SONAR). In some embodiments, a physical parameter detected by the sensor 10 may include repetitive features of a CC or a MSKC, as shown in FIGS. 4 and 6. In some embodiments, the features useful for identifying the CC pump timing may correspond to an ECG R-wave, an ECG T-wave, an end of the ECG T-wave, a peak of a cardiovascular systolic pressure, a nadir of a diastolic cardiovascular pressure, and/or a transition point in a cardiovascular pressure of the user, as shown in FIG. 4. These features and their respective timings may be identified from the raw signals by processing algorithms programmed into processor 11, or alternatively the feature identification process may be incorporated into the sensing device directly. Similarly, features useful for identifying the MSKC pump timing may be determined using algorithms programmed into the processor 11 from raw signals sensed by one or more sensors 10 (e.g. 10b), or alternatively incorporated into the sensing device directly.

As described herein, a signal may include two or more characteristics. In some embodiments, a first characteristic of a signal may include a repetitive feature of a CC, for example a T-wave or an R-wave of the electrical signal of the CC or a peak pressure of a plethysmography signal, and a second characteristic of the signal may include a repetitive feature of a musculoskeletal activity, for example a step timing of a user. In some embodiments, two or more characteristics may be derived using processor 11 from one signal. For example at least one of HR and MSKR and MSKR to CC relative timing information may be derived from characteristics of a signal from the same plethysmogram or a plethysmographic sensor 10.

In some embodiments, as shown in FIGS. 1 and 2, a user input interface 12 may receive information from the processor 11. The user input interface 12 may be configured to receive commands or cues from a user that are delivered to the processor/controller 11, as well as configured to deliver commands or cues from the processor/controller to a user or device/component. Commands may be tactile, audio, visual, or in any other form. In some embodiments, tactile commands from the user may include keypad strokes, actuation of switches or buttons, and/or touch interactions delivered by the user. Additionally, vibrations, taps, electrical signals, or nudges are examples of commands that may be provided to the user from the system. Audio commands may include those received by the user input interface 12 from the user, the processor 11, the sensors 10, or the user guidance interface 13. Further, audio commands delivered to the user may include commands that direct the MSK activity of the user, including, for example, a metronome, the beat of music, drum beats, changes in tonal qualities of an audible prompt, and/or games and words. In some embodiments, visual commands or cues may include visual displays or prompts, analogue dials, graphs, movies, games, or any other type of viewable command. In certain embodiments, tactile guidance may include at least one of guidance on a timing, location, magnitude, and/or direction of MSK activity, using one or more separate means or skin locations for stimulating the user. For example, a mechanical or electrical tactile prompt may be provided to one or more locations on the user's hand, wrist, head, or foot, depending on the placement of the prompt device. In further embodiments, the magnitude, quality, or location of the prompt may be varied so as to guide the user's MSK activity, for example, to guide at least one of a user's speed, effort, or direction while walking or running.

As shown in FIG. 1, a system may include a user guidance interface 13. In some embodiments, the user guidance interface 13 may be combined or merged with the user input interface 12, such that the user input interface 12 is the user guidance interface 13. Alternatively, the user guidance interface 13 may be combined or merged with an equipment interface 14, as shown in FIG. 2, such that the equipment interface 14 is the user guidance interface 13. As described herein, guidance includes enabling a user to obtain and maintain a target MSKC to CC timing relationship.

In some embodiments, the user guidance interface 13 may include a prompt device that provides a recurrent prompt (guidance) at a prompt rate to the user as a timing indication for performance of the rhythmic musculoskeletal activity. The prompt device may be controlled by the processor 11. In some embodiments, the prompt rate may be substantially equal to a HR or a cadence of a user. In other embodiments, a HR of the user may be substantially an integer multiple of the prompt rate. In some embodiments, predetermined target cadences or prompt rates may be available to a user. For example, the target cadences (i.e. to achieve the target MSKC to CC timing relationship) may be based on a user's natural or preferred cadences, type of activity (e.g. walking vs. jogging vs. running a competitive 5 K), duration of activity, gender, age, fitness level, other demographic information, user anatomy (e.g. height, weight), or other diagnostic information.

Timing of guidance signals may initiate automatically, by user request through a user input interface 12 when HR and MSKC timing are nearly aligned, or the user may be signaled or reminded when the guidance is available or appropriate through user input interface 12. The guidance may be recurrent. In some embodiments, the guidance may fade away or become imperceptible as long as the user achieves and maintains the target MSKC to CC timing relationship. The guidance may resurface or become perceptible if the user fails to sustain the target MSKC to CC timing relationship during a given time period. In some embodiments, the system senses that a user responds late or early to guidance and adjusts the guidance automatically to guide the user to the target MSKC to CC timing relationship. Alternatively, in some embodiments, a user may adjust the guidance manually, for example to increase or decrease a target MSKR or HR, such that the target MSKC to CC timing relationship dictated by the system is reset accordingly.

In some embodiments, the user guidance interface 13 of the system may include music to guide the MSKC timing of the user. Accordingly, a user may be prompted with music having a beat that will guide the user to a target MSKC to CC timing relationship. Music may be selected in real-time, pre-selected, or automatically selected, for example, in response to the measured or known beat frequency of the songs and the actual or target MSKR of the user. Playlists or sequences of musical renditions may be defined by the user, or suggested by the system to the user. Playlists may vary depending on the HR, MSK activity, and other states desired for a given physical activity. Musical selections used to prompt MSK activity timing may change in beat frequency, beat volume relative to overall music volume (e.g. drum beat, base guitar, concurrent metronome), overall music volume, or other features to guide the user. In an exemplary embodiment wherein a drum beat of a musical track is the timing prompt for a user, the volume of the drum beat prompt relative to the volume of the musical track may gradually increase above a baseline or added on top of a the track, as the accuracy or consistency of the user's timing relative to the prompt decreases. Alternatively, the volume of the drum beat prompt relative to the remainder of the musical track may decrease or return to a baseline in response to a sustained improvement in the user's MSKC timing accuracy or consistency. In certain embodiments, the system may further be configured to constantly adjust the playback speed of the music to fine-tune the beat rate used to guide the user. Additionally, the music with altered playback speed can be pitch-corrected to maintain the proper intonation.

In some embodiments, the system may deliver a new prompt or modify an existing prompt in order to indicate to the user the need to more accurately or consistently step to the underlying beat of the delivered music and/or the need to make corrections in MSK activity such as changes to stride length, degree of knee bend, heel strike, toe-off, exercise resistance, bicycle gear, or arm swing. In some embodiments, a user may hear a change in prominence of the underlying beat of a song (for example the base drum, base guitar, and/or an added metronome beat) relative to the rest of the song as an indication to the user that he or she needs to more accurately move with the timing of the underlying beat of the music, improve identification of the prompt within the music, or pay better attention to moving to the beat. Musical communication may be pre-defined by the user so as to suit his or her understanding or preferences. A tactile prompt can be provided at a prompt rate in addition to or instead of an audible prompt.

In some embodiments, guidance may be provided by game embodiments that utilize metrics. For example, one embodiment of the system includes sensors that continuously run in the background during any rhythmic physical activity. In this embodiment, information from sensors and/or MSK activity guidance may be offered, made available, or automatically turned on as a biofeedback prompt when, during the course of that activity, the HR naturally approaches or approximates an integer multiple of the MSKR of the user (e.g. 1×, 2×, 3× . . . ). For example, biofeedback may be provided audibly via an earbud or other earpiece; visually via head-mounted smart eyeglasses or contact lenses or a smart-watch; via tactile feedback from a smart-watch, smart-headset, or smart-shoe; or via any other type of biofeedback enabled device, as described herein.

Games and gaming systems may be leveraged, including, for example, an Xbox Kinect type audio-visual gaming hardware that includes cameras that can visualize at least one of the MSKC and the CC of the user, as well as provide at least one of audio, visual, and tactile MSKC timing guidance to the user. In embodiments of the system and method, MSKC timing inputs may be received and/or captured by a camera(s), such that the camera(s) may capture other MSK activities beyond foot strike timing and/or arm motion timing. Further, CC timing inputs may be acquired by gaming sensors. For example, a camera may be used to monitor CC timing via at least one of subtle rhythmic skin color changes, small temperature (IR) changes, and tiny rhythmic movements (e.g. head bobbing) caused by arterial blood flow and pulsatile pressure changes during the CC. Gaming system embodiments may include wearable sensors for ambulatory versions, whereas a video camera(s) may enable sensing of MSKC timing without wearable sensors. Alternatively, an accelerometer, other position/orientation sensors, floor based pressure sensors, or EMG may be used to measure the whole body or specific limbs or muscles, such as number of muscles, force of contractions, magnitude and/or speed and/or acceleration of movement that achieves the target MSKC to CC timing relationship. A game may be configured to give points or other scalable credit for increases in well-timed physical activity metrics relative to timing targets, including foot strike, limb movement metrics, and other body movement metrics. Limb movement metrics may include speed, acceleration, change in center of mass, or body movement. Body movement metrics may include speed, acceleration, center of mass, side-to-side movement, or change in height.

Figure 11:
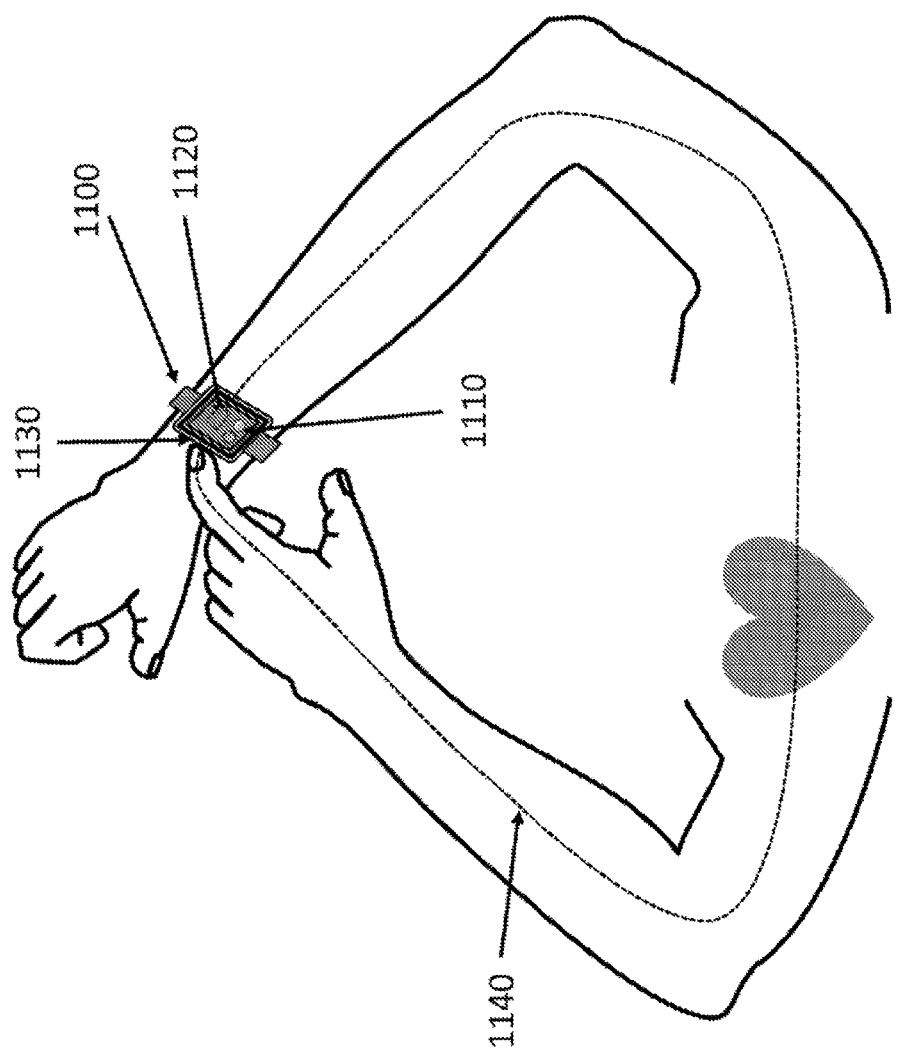
FIG. 11 illustrates a wrist-based device for calibration of a CC sensor, in accordance with a preferred embodiment.
Figure 12:
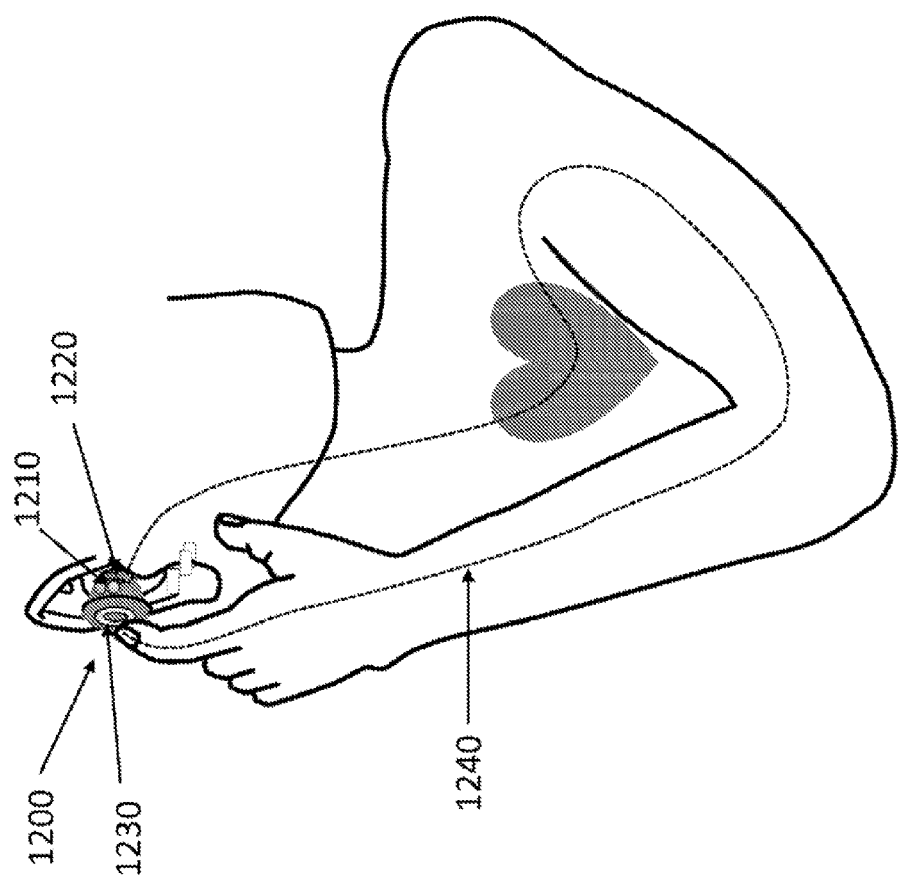
FIG. 12 illustrates a head-based device for calibration of a CC sensor, in accordance with an alternative preferred embodiment.

Algorithms used by the system for determining a user's actual CC timing may include calibration or corrections for arterial pulse transit time related to at least one of the user's height, age, HR, pulse amplitude, or a CC measurement location, for example. Acquisition of CC timing may include analysis and/or amplification of plethysmographic signals, skin color changes, and/or head movements (e.g. following set points on face of the user) related to the pulsatile flow of arterial blood. Alternatively or additionally, acquisition of CC timing may include information from other sensors and wearable devices, for example, an ECG. As illustrated in FIGS. 11 and 12, an ECG signal may be obtained simultaneously with an arterial pulse signal, enabling calibration of the pulse transit delays in monitoring the CC timing, because the heart's electrical activity (ECG) reliably reflects the true timing of the CC due to the speed with which electrical signals travel through the body, while pulse pressure signals travel much more slowly at variable speeds that are effected by user size, age, arterial anatomy, sensor placement, and cardiovascular physiology (e.g. cardiac contraction force, blood pressure, hyrdration, blood viscocity, temperature, vasoconstriction, arterial wall stiffness, etc.)

Figure 3A:
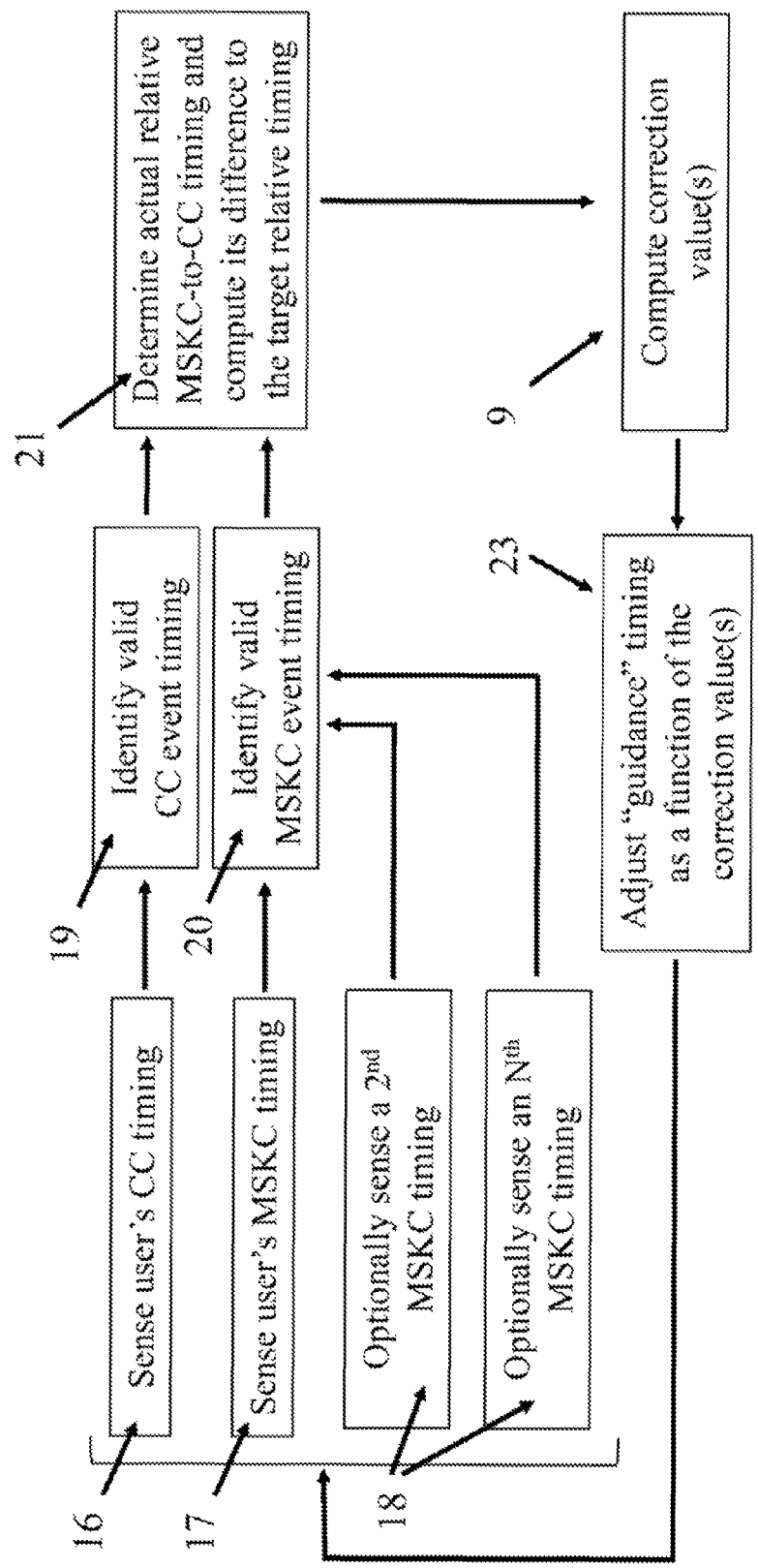
FIGS. 3A-B illustrate flow charts for sensing, calculating, and guiding a CC and MSKC timing relationship(s) of a user, in accordance with certain preferred embodiments.
Figure 3B:
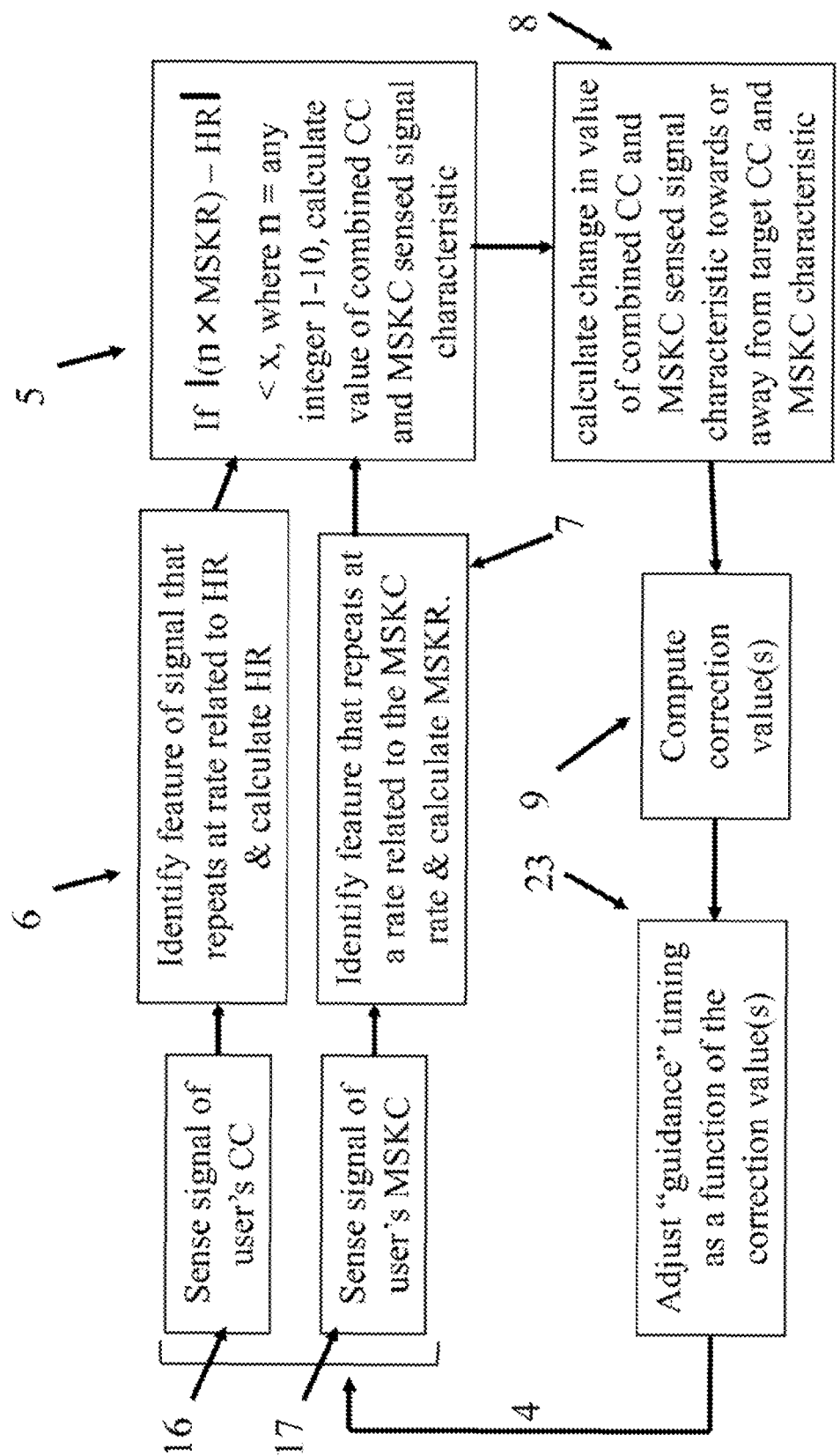

Methods of Using Sensor Technologies for Favorably Coordinating CC and MSKC Timing FIGS. 3A-B illustrate flow diagrams of a system in accordance with preferred embodiments that include sensing a CC and MSKC timing of a user. As shown in FIGS. 3A-B, the system senses CC timing 16 and MSKC timing 17 of a user. Any number of sensing technologies may be used, for example ECG or plethysmography can be used to sense CC timing. Optionally, as shown in FIG. 3A, additional (e.g. $2^{nd}$, $3^{rd}$, $4^{th}$, $N^{th}$) MKSC timings 18 of a user may be sensed by the system, each being compared in step 21 to the CC timing of the user and/or to each other.

FIG. 3A illustrates a flow diagram for sensing a CC and MSKC timing of a user, for example using ECG and an accelerometer. As shown in FIG. 3A, a processor is used to identify a valid CC 19 and a valid MSKC 20 event timing. A valid CC event 19 may be any point or portion of a CC or other information that conveys CC timing information, as discussed above. A valid MSKC event 20 may be any point or portion of a rhythmic physical activity that conveys MSKC timing information, as discussed above. Valid events 19 and 20 may correspond to those that pass signal processing metrics designed to reject false events caused by noise or other interferences that are unrelated to the user's heartbeat or relevant MSK activity. For example, detected events in the CC signal that occur too soon after a previous valid CC event and that would otherwise represent a non-physiologic HR or one that is far greater than the user's recent valid HR may be rejected.

In some embodiments, an actual (e.g. real-time) relative MSKC to CC timing is determined and compared to a target relative MSKC to CC timing 21. The difference between the actual relative MSKC to CC timing and the target MSKC to CC timing 21 is calculated, representing a difference value in a feedback loop, which is used to determine a correction, if needed, in any guidance a user requires to achieve the target MSKC to CC timing relationship. In some embodiments, the timing relationship between the first MSKC timing and the second MSKC timing may be obtained using a first processor. Further, in some embodiments, the timing relationship between the second sensed MSKC timing and the CC timing may be obtained by the same first processor or on a second processor. Each MSKC to CC and MSKC to MSKC timing relationship is characterized by the elapsed time between the occurrence of one component of the first signal and the occurrence of one component of the second signal. In some embodiments, this timing relationship may further be normalized (i.e., divided) by the elapsed time between two subsequent occurrences of the one component in the first or second signal. Additionally, in some embodiments, the timing relationships may be recalculated on a continuous real-time basis, at random times, or at various intervals.

In some embodiments, correction values 9 may be computed to adjust the timing of the guidance as a function of the correction values. The correction values may be based on the CC timing of the user, the first or second MSKC timings of the user, a relative MSKC to CC timing, the difference to a target MSKC to CC timing relationship, or one or more time delays, offsets, or other information. Further, a user may be guided or prompted to achieve the target MSKC to CC timing relationship based on the adjusted timing of the guidance 23. In some embodiments, the flow diagrams of FIGS. 3A and 3B may repeat in a loop function. Alternatively, the user may achieve and maintain the target MSKC to CC timing relationship, and thus not require any adjustment in the guidance. In some embodiments, the loop function may be used to calibrate a system to one or more physiological preferences of a user, as will be described below. For example, the system may adjust the guidance to a user that steps early or late relative to a target MSKC to CC timing relationship upon receiving the guidance. Alternatively, a user may naturally achieve MCP occasionally during certain rhythmic musculoskeletal activities. Thus, the system may be calibrated to adjust the guidance to enable the user to maintain the natural MCP of the user.

FIG. 3B illustrates a flow diagram for sensing a CC and MSKC timing of a user, for example with PPG or IPG, in accordance with a preferred embodiment. As shown in FIG. 3B, the system may sense a signal from a sensor 16 that correlates to the CC of a user to calculate a HR 6, and another signal of the user using a sensor 17 that correlates with the MSKC 17 in order to calculate an MSKC rate (MSKR), using any number of sensing technologies. In some embodiments, signals that correlate to both the CC and MSKC of a user may be obtained from a single sensor, 16 or 17. For example, as will be described more fully below, a plethysmographic sensor can be used to sense one or more of CC timing, MSKC timing, and information regarding MSKC to CC timing relationships. In some embodiments, the timing relationships may be recalculated on a continuous real-time basis, at random times, or at various intervals.

In some embodiments, as shown in FIG. 3B, if the HR of the user approaches an integer multiple of the MSKR ((n×MSKR)–HR, where n=any integer 1-10) of the user (with an absolute difference <x per minute) 5, then a characteristic (or set of characteristics) of the sensor signal can be used to guide the user towards a target MSKC to CC timing relationship. For example, the sensor signal may be a PPG and the characteristic may be pulse amplitude in the PPG or, in another embodiment, a combined measure of pulse amplitude and pulse complexity. The change in the value of the characteristic that represents the MSKC to CC timing relationship may be calculated to determine an amount and nature of guidance a user requires to achieve the target MSKC to CC timing relationship 8, as will be described in further detail in association with FIGS. 6-7. In some embodiments, correction values 9 may be computed to adjust the timing of the guidance as a function of the correction values. A user may be guided or prompted to achieve the target MSKC to CC timing relationship based on the adjusted timing of the guidance 23. In other embodiments, as described later in FIG. 7, the MSKC timing may be held constant and the user may be guided to the target MSKC to CC timing relationship by guiding changes in CC timing by guiding changes in the effort invested in the MSK activity, e.g. changes in MSKC speed, acceleration, power, resistance, stride length, or incline during exercise. In some embodiments, the flow diagram of FIG. 3B may repeat in a loop function 4, as described above. Alternatively, the user may achieve and maintain the target MSKC to CC timing relationship, and thus not require any adjustment in guidance. In some embodiments, the loop function may be used to calibrate a system to one or more physiological preferences of a user, as will be described below.

In accordance with the description above, FIGS. 4A-C illustrate a timing relationship between central arterial pressure waveforms, peripheral arterial pressure waveforms, an electrocardiogram tracing, a targeted musculoskeletal contraction cycle, and a timing of sensed MSKC events of a user, in accordance with preferred embodiments. FIGS. 4A-C are shown aligned horizontally in time to each other for the purpose of illustration, such that the information has been sensed, detected, or collected by one or more sensors or sensor technologies as described above and processed by a processor. The sensed timing relationships, as shown in FIGS. 4B and 4C, may be used to determine the MSKC to CC timing relationship of a user. In general, central arterial waveform 32 represents exemplary arterial pressure in the aorta of an individual at rest, while waveform 34 represents at least one of an exemplary simultaneous peripheral arterial pressure, flow, and/or volume (e.g. peripheral PPG or blood pressure signal) of the same individual. As shown in FIG. 4A, simultaneously monitored exemplary central arterial pressure waves 32 and peripheral arterial pressure waves 34 are temporally offset from one another due to arterial pulse transit time, the time required for the arterial pressure waves to propagate through the arterial circulation from the heart and central circulation to a given peripheral location in the body of the user. Each of these waveforms exhibit changes in arterial pressure caused by the systolic 25 and diastolic 29 portions of the CC, which may include a peak systolic pressure 31, that repeats at the HR of the user.

Further, as shown in a simultaneous electrocardiogram (ECG) tracing in FIG. 4B, the representative ECG signal 22 (illustrative of the tracing one might obtain, for example, from a chest strap lead), includes various different waves including P-waves, Q-waves, R-waves, S-waves, and T-waves. R-waves 24 (24a, 24b, and 24c) represent depolarization of the ventricular muscle of the heart. R-waves 24 repeat with each heartbeat at a HR of a user and are readily identifiable in an ECG signal 22. Therefore, in some embodiments, R-waves 24 may be utilized in the measurement of the HR via the measurement of the duration of R-to-R intervals (RRI) 26. The T-wave 28 reflects ventricular repolarization. End T-wave 30 may be used as a marker of the approximate timing of aortic valve closure, which marks the beginning of diastole during the pumping cycle of the heart. The timing and characteristics of these waves in FIGS. 4A-B, like other similarly sensed waves and wave markers, are representative of the timing of the CC and therefore may be used in calibrating, guiding, and/or tracking a user and to coordinate MSKC and CC hemodynamics to achieve a target MSKC to CC timing relationship.

As shown in FIG. 4C, skeletal muscle contraction cycles 36 include periods of relaxation and contraction, as indicated by the dotted lines in FIG. 4C and, with respect to the timing of a user's CC shown in FIGS. 4A and 4B above, may include a target MSKC to CC timing relationship, in accordance with embodiments of the methods and systems. While exemplary skeletal muscle contraction/relaxation cycles 36 and prompts 35 are illustrated in FIG. 4C, arterial and venous MSK induced blood pumping also may be caused by changes in inertia during many types of rhythmic physical activity. Also, while exemplary central 39 and peripheral 40 arterial waveforms are illustrated in FIG. 4C, other important factors in optimizing MSKC blood pumping and target MSKC to CC timing relationships during many types of physical activity may take place but are not illustrated by the arterial waveform, for example venous blood pumping from MSKC induced skeletal muscle pumping.

As is illustrated in FIG. 4C, both the CC and MSKC pressure waves can be sensed simultaneously by a sensor responsive to changes in the arterial blood pressure, volume, or flow. Further, as is illustrated in FIG. 4C, when HR and MSKR are equal, then the MSKC may create pressure waves within the arterial circulation that are substantially at the same frequency as the pressure waves created by the CC. Exemplary arterial pressure waveform 39 represents an approximation of the central arterial pressure during MCP, wherein maximal MSK induced blood pumping is seen in the central arterial circulation during early diastole. This same waveform 39, however, may also represent an approximation of the peripheral arterial pressure, for example at the head of a user, during MSK-induced iMCP due to inertial effects and/or the impact of pulse transit time on arterial waveform shape and timing. Waveform 39, when observed centrally during MCP, may be very similar in appearance to the central waveform that can be produced during other types of medically induced therapeutic counterpulsation techniques, including intra-aortic balloon counterpulsation (IABP) and external counterpulsation (ECP). Waveform 39 may also illustrate the shape of a target peripheral arterial waveform during ECP and IABP counterpulsation, because, with the user at rest, the pressure flow waves created by the two favorably coordinated pumps (e.g. CC & ECP pumps) can maintain their relationship to one another as the waves propagate through the circulation of the user. Further, an exemplary peripheral arterial pressure waveform 40, as might be sensed from a location on the head of a user during MCP is illustrated, which also represents an approximation of an exemplary central arterial waveform during iMCP.

Because physical activity can cause blood pumping via both MSK contraction/relaxation cycles and through changes in inertia, the location of an arterial sensor can be important in determining the waveform timing characteristics of the waves created by each of these separate pumping mechanisms. For example, (1) pulse transit time from a CC is increased with the arterial distance of the sensor from the heart; (2) pulse transit time from a skeletal muscle contraction pumping location is also increased with the arterial distance from the skeletal muscle doing the pumping; while (3) the inertial pump waveforms occur concurrently with the changes in inertia that create them, but their amplitude and direction can be dramatically effected in their relationship to skeletal muscle pump and the CC pump waveforms by the location of the sensor, for example, at, above, or below the heart and/or skeletal muscle pump (e.g. sensor at head vs. chest vs. foot of the user during running) or in other examples, on a limb held substantially parallel to the ground vs. one held substantially perpendicular to the ground in one direction vs. one held substantially perpendicular to the ground in the opposite direction (e.g. wrist based sensor with hands held above the head vs. hands kept at lower chest vs. hands kept below the waist during running). Because wave amplitude and timing in response to a CC and MSKC can change with different activities and physiologies and sensor locations, calibration of the system to user, physiological variables, sensor location, and specific physical activity can be important.

As shown in FIG. 4C, examples of target MSKC to CC timing relationships are illustrated, comprising periods of skeletal muscle contraction during central diastole 29, as shown in FIG. 4A, followed by periods of relaxation during central systole 25. In exemplary target MSKC to CC timing relationship 36, the user has been guided to perform the portion of the rhythmic MSK activity that results in maximal MSKC blood pumping to begin at timing prompts 35 (black triangles) that repeat with each instance of the CC such that the ratio of MSKC:CC occurrences is 1:1. Alternatively, the MSKC prompts may be timed at the same location in the CC, but less frequently (e.g. with every other CC (1:2), every third CC (1:3), or every fourth CC (1:4)), wherein the HR is an integer multiple of the MSKR. As shown in FIG. 4B, % R-R interval scale 38 provides a graphical representation of the percent of the R-to-R interval (RRI) 26 nomenclature, one RRI representing one full CC. % RRI may be computed as the amount of time between an MSKC event and the most recent prior CC event, divided by the amount of time between successive CC events, multiplied by 100. For example, 0% and 100% of the RRI represent the timing of the R-waves (e.g. 24a, 24b, 24c, etc.) in the CC, while 25% of the RRI is a quarter of the way between successive R-waves, and 50% is the mid-point between two sequential R-waves 24 of a CC. Scale 38 of the RRI may alternatively be expressed fractionally as a value from zero to one, in units of degrees between zero and 360 degrees, or in radians between zero and $2\pi$ radians (e.g., 25%=0.25=90 degrees=1.57 radians), equivalent to the percentage terminology. Values greater than 100% describe events in a subsequent RRI (e.g., 130% represents a 30% location in the following interval). Thus, the RRI may be used to align prompts and musculoskeletal contractions within the same location of each CC over time.

In some embodiments, multiple MSK activities, involving different muscle groups across the user's body, may be performed simultaneously or sequentially by a user, with each of these activities having its own MSKC timing and either a shared or unique target MSKC to CC timing relationship. In such a scenario, the relative timing of each MSKC to CC may confer separate cumulative hemodynamic effects on the central and peripheral circulation of a user, thereby impacting the magnitude of overall MCP or iMCP. MCP is considered optimized for a rhythmic physical activity when the CC and the MSKC are favorably coordinated so as to generate early diastolic pressure waves in the central circulation similar to those of waveform 39 in FIG. 4C. In some embodiments, it may be preferred to vary the target MSKC to CC timing relationship to optimize hemodynamics for different simultaneous or sequential MSK activities. Further, guiding a user to accomplish MCP or other MSKC to CC timing relationships may be desired, for example, in order to alter blood flow to specific MSK or non-MSK tissues, for example to improve cerebral perfusion.

Figure 5:
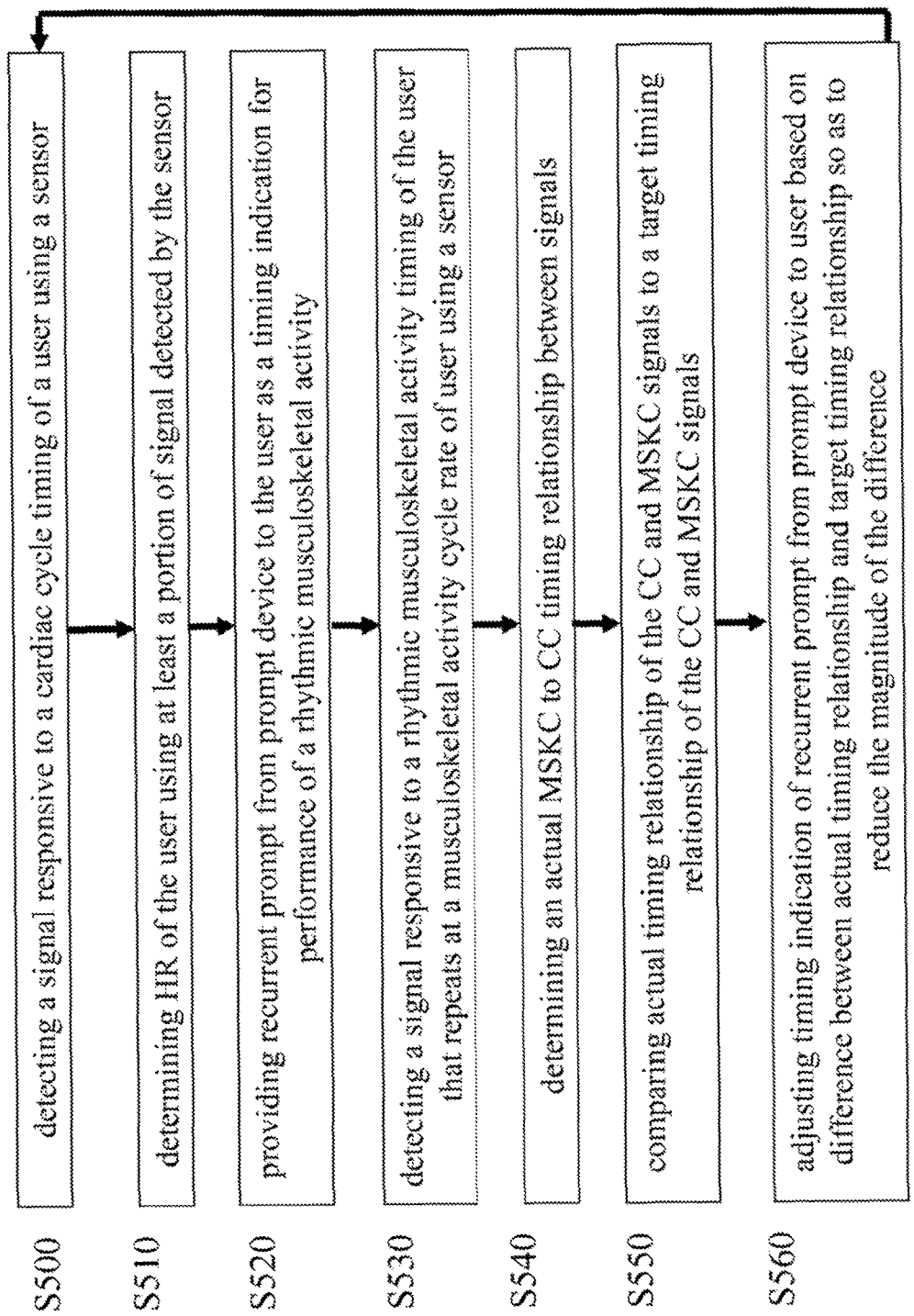
FIG. 5 illustrates a flow chart for guiding a user to a target MSKC to CC timing relationship using a CC sensor (e.g. an electrocardiogram) and an MSKC sensor (e.g. an accelerometer), in accordance with a preferred embodiment.

FIG. 5 illustrates a flow chart for guiding a user to a target MSKC to CC timing relationship. A method for guiding a user to a target MSKC to CC timing relationship of a preferred embodiment includes detecting a first signal responsive to a CC timing of a user using a first sensor S500; determining a HR of the user using a at least a portion of the first signal detected by the sensor S510; providing a recurrent prompt from a prompt device to the user as a timing indication for performance of a rhythmic MSK activity S520; detecting a second signal responsive to a rhythmic MSK timing of the user that repeats at a musculoskeletal activity cycle rate (MSKR) of the user using a second sensor S30; determining an actual MSKC to CC timing relationship between MSKC and CC signals S540; comparing the actual timing relationship of the CC and MSKC signals to a target timing relationship of the CC and MSKC signals S550; and adjusting the timing indication of the recurrent prompt from the prompt device to the user based on the difference between the actual timing relationship and the target timing relationship so as to reduce the magnitude of the difference S560. The method repeats by looping back from step S560 to S500, with the net effect of recurrently prompting and guiding the user so as to reduce the magnitude of the difference. In some embodiments, the method preferably uses an accelerometer and an ECG to determine actual and, in some embodiments, target MSKC to CC timing relationships of a user, although any CC and MSKC sensor or sensor combination may be used as described above in connection with FIGS. 1 and 2.

As shown in FIG. 5, step S500 includes detecting a first signal responsive to a CC timing of a user using a first sensor. Further, step S510 includes determining a HR of the user using at least a portion of the first signal detected by the first sensor. In some embodiments, a CC signal, or a portion of the cardiac signal, may include any recurrent aspect or feature of a CC, as described above, for example an R-wave of an ECG, a systolic peak of a plethysmogram, or a Fourier transform of either of these exemplary signals.

As shown in FIG. 5, step S520 includes providing a recurrent prompt from a prompt device to the user as a timing indication for performance of a rhythmic MSK activity. In some embodiments, the recurrent prompt repeats at a prompt rate such that the HR is substantially an integer multiple of the prompt rate.

As shown in FIG. 5, step S530 includes detecting a signal responsive to a rhythmic MSK timing of the user that repeats at a MSKR of the user using a second sensor. Step S530 functions to determine a MSKC timing of a user, such that an actual MSKC to CC timing relationship may be calculated as shown in step S540. In some embodiments, one or more sensors, for example an accelerometer, EMG, or any position/orientation sensor, may be used to sense aspects of an MSKC of a user, such that an actual MSKC to CC timing relationship may be calculated. For example, maximal MSK muscle contraction may be synchronized with the beginning of diastole in the CC of the user, as shown in FIGS. 4A-C. In some embodiments, step S530 may further include determining the MSKR of the user using the data from the second sensor with a processor. In some embodiments, the sensor used to sense the CC of a user (S500) may be the same sensor used to sense the MSKC (S530) of the user. Alternatively, two or more different sensors may be used to determine a CC and MSKC of the user.

As shown in FIG. 5, step S540 includes determining the actual MSKC to CC timing relationship between first and second signals. The actual timing relationship may be the measured timing relationship between the MSKC timing and the CC timing. For example, the actual MSKC to CC timing relationship of a user may correspond to MCP, to iMCP, or somewhere in between. Generally, most users not prompted to do otherwise will unintentionally vary in their MSKC to CC timing relationships during a rhythmic MSK activity.

As shown in FIG. 5, step S550 includes comparing an actual timing relationship of the CC and MSKC signals determined in step S540 to a target timing relationship of the CC and MSKC. Step S550 preferably utilizes a target MSKC to CC timing relationship that enables a user to achieve MCP. In some embodiments, the target MSKC to CC timing relationship of a user may correspond to a condition when the CC and the MSKC blood pumps work in a complimentary fashion. In certain other embodiments, a target MSKC to CC timing relationship for a user may correspond to, for example, simply avoiding persistent alignment of maximal MSKC blood pumping of the user with a peak of a systolic arterial pressure signal of the user so as to prevent the two pumping systems from persistently working against each other.

As shown in FIG. 5, step S560 includes adjusting a timing indication of a recurrent prompt from the prompt device to the user based on a difference between the actual timing relationship and the target timing relationship so as to reduce the magnitude of the difference. Step S560 preferably functions to guide the user towards the target MSKC to CC timing relationship. As shown in FIG. 5, step S560 loops back to step S500 so as to repetitively update the recurrent prompt and guide the user towards substantially obtaining and maintaining the target MSKC to CC timing relationship. In some embodiments, if the actual MSKC to CC timing relationship of the user determined in S540 is associated with MCP (the target relationship of S550), the system functions to provide a recurrent prompt to the user that maintains the user at that timing relationship. In some embodiments, the recurrent prompt provided in S520 may comprise an audible or tactile metronome beat or a musical beat, wherein the beat frequency corresponds to the prompt rate. Furthermore, the prompt rate may continue persistently at the same frequency when in step S560 no adjustments to the prompt timing are indicated or for up to a pre-defined period of time when signals from S500 and/or S530 and the computations of S540 become temporarily disrupted.

FIGS. 6A-G illustrate a series of PPG signals of a user 41, 42, 43, 46, 47 and 610, in accordance with a preferred embodiment. As described above, sensors utilizing plethysmography (e.g. PPG or IPG) may be used within a system to favorably coordinate a timing of a rhythmic MSKC of a user that repeats at a MSKR of the user with a timing of a CC of the user that repeats at a HR of the user. In general, plethysmography signals from a blood-perfused tissue include a pulsatile component ("AC") and a non-pulsatile component ("DC"), reflecting the short-term time varying changes in local blood volume and overall raw signal levels, respectively. As is the case in FIGS. 6A-G, plethysmography signals are typically presented graphically after normalizing (dividing) the signal by the recent average DC values to remove the influence of factors unrelated to the blood volume changes. The signal's "pulse amplitude" (PA=100× AC/DC as a percentage, sometimes also referred to as percent modulation amplitude or perfusion index) is an indicator of pulsatile signal strength and correlates to the relative changes in blood volume in the underlying tissue. For example, the pulse amplitudes of the PPG signals plotted in FIGS. 6A-F vary between approximately 2% and 6%, corresponding to the peak-to-valley heights of the envelope.

In some embodiments, plethysmography may be used collectively to determine at least one of a CC rate, a CC timing, an MSKR, an MSKC timing, a MSKC to CC arterial blood flow or pressure interaction, a MSKC to CC timing relationship, a target MSKC to CC timing waveform, and a target MSKC to CC timing relationship, and may function to guide a user to a target MSKC to CC timing relationship. For example, a sensor of blood volume, pressure, or flow, such as a PPG sensor, may be used alone or in combination with one or more additional CC or MSKC sensors to provide reliable identification, achievement, and maintenance of a target MSKC to CC timing relationship. For example, to derive a HR of a user using a PPG sensor alone, instances of at least one feature of the PPG signal that repeats at the HR of the user (e.g. peak regularly occurring signal amplitude, P, illustrated by peaks 31 in FIGS. 4A, 4C, and 6D) may be identified by a processor, with HR calculated from the recurring time interval between each instance (the heart's beat-to-beat or P-to-P interval), wherein HR=heartbeats/minute=[1 minute÷(beat-to-beat interval in minutes)].

In some embodiments, the same PPG signal may also be used to derive the MSKR during rhythmic physical activity by identifying instances of one or more features of the MSKC and CC wave interaction patterns in the PPG signal. For example, when two waves in the same system occur at different but similar frequencies, a characteristic beat pattern (FIG. 6A) may be created in which the waves repeatedly go back and forth between overlapping 46 (resonance) and separating 47, with a maximal beat wave amplitude happening when the two waves occur at the same time in the same location 46. In the event that the MSKC induced arterial pressure waves are from a single predominant rhythmic MSK pump, the resulting recurring increase and decrease in beat wave amplitude occurs at a beat frequency that is the difference in the frequency between the two separate recurring CC and MSKC induced waves. Therefore, once the HR has been calculated from data obtained via the PPG signal (as described, or via one or more other CC sensor systems), the MSKC frequency may be calculated by adding or subtracting the beat frequency of the PPG, which may be possible if the HR and MSKR are close enough to one another that the beat pattern of the overlapping MSKC and CC waves is identifiable. There are multiple simple ways to determine whether the beat frequency should be added or subtracted from the HR, for example, the wave morphology as seen in an asymmetrical shape of the beat pattern of the PPG, as shown in FIG. 6A, may be reversed when the MSKR is higher than the HR. Alternatively, an additional sensor, such as an accelerometer, may be used to identify a separate MSKR signal, which will be described in further detail below. In some embodiments, the relative timing, shape, and magnitude of the signals from pressure, volume, or flow sensors at different anatomical locations vary due to pulse transit times (on the order of tens to hundreds of milliseconds), with a magnitude that generally increases as a function of the sensor's distance from the blood pump that has generated the sensed change in signal. Conversely, electrical sensors (e.g. ECG, EMG, EEG) sense electrical signals that travel from their sources at nearly the speed of light. Thus, delays due to anatomical location are imperceptible and clinically irrelevant. The increase in the magnitude of the delay (pulse transit time) with the distance from the heart to the peripheral location at which the waveform is measured, means that, for example, an increase in the size of the individual (e.g. height or length of limb for a limb-based plethysmographic sensor) might be a factor in generally increasing pulse transit time in that individual over individuals of smaller size, all else being equal. Other factors may also influence arterial pulse transit time delays and wave morphologies, including vascular attributes (e.g. arterial stiffness, size), the type of MSK activity, blood effects (e.g. volume, viscosity), and cardiac effects (e.g., contractility). These pulse transit time delays and other offsets may be accounted for in determining a target MSKC to CC timing relationship and/or in computing an actual MSKC to CC timing relationship.

FIG. 6A illustrates an exemplary PPG signal 41 observed at the forehead of a user running at a step rate slightly slower than the HR of the user. The slightly slower step rate of the user results in the user stepping, on average, slightly later in the CC with each step, as indicated by the points in 44 which indicate the MSKC to CC timing as a % RRI (0-100%) of each step of the user. As shown in FIG. 6A, the different contributing wave frequencies combine in the PPG to yield the observed beat phenomenon, wherein the peak arterial blood volume waves regularly oscillate in magnitude between maximal 46 and minimal 47 size at a rate per minute equal to the difference between the HR and the step rate. In some embodiments, beat phenomenon 46-47 is a result of the regular, simultaneous occurrence of separate arterial pressure wave peaks from MSK activity vascular pumping and the CC pumping. These separate pressure waves, created at different frequencies, cycle between being substantially separate 47 to being progressively more on top of one another and therefore substantially combined 46 then back again, repetitively, leading to regular oscillations in the magnitude of the periodic arterial blood volume, as shown in FIGS. 6A, D, F. Further, the frequency of the beat phenomenon may also be used as an input into a program or delivered to a processor that calculates the step rate once the HR is known, or calculates the HR once the step rate is known (e.g. from a separate accelerometer signal).

Further, additional characteristics of the PPG wave may reflect the actual timing of the MSKC relative to the timing of the CC. In some embodiments, signals may be processed to identify target PPG waveform characteristics and patterns that correspond to desired MSKC to CC timing relationships. For example, values that represent PPG morphology, overall DC signal amplitude, pulse amplitude, average amplitude, changes in amplitude, rates of changes in amplitude, and averages and progressions thereof, may be provided to a processor where they may be used to calculate a correction value for adjusting guidance to a user that, when generally followed by the user, functions to reduce the difference between the actual MSKC to CC timing relationship and the preferred MSKC to CC timing relationship. In one embodiment, a processor may initially calculate appropriate guidance of timing to guide the user to achieve an MSKC rate (e.g. step rate) that is substantially equal to HR. In another embodiment, such initial guidance is not provided, and the system initiates guidance once the PPG signal begins to exhibit general behaviors chosen as indicators that a preferred MSKC to CC timing would be readily achievable with user guidance.

In some embodiments, as shown in FIG. 6A, a periodic change in pulse amplitude of the PPG waveform may be present, indicating that the user is stepping at a timing relative to the CC timing that slowly changes over time during the rhythmic musculoskeletal activity. The processor may identify one or more characteristics of the PPG waveform that correlate with relative MSKC to CC timing (e.g.

pulse amplitude), while simultaneously identifying a marker of optimal relative MSKC to CC timing, for example a reduced or minimum HR ($HR_{min}$) when compared to HR during an alternative MSKC to CC timing. As shown in the exemplary PPG signals in FIG. 6C when the PPG amplitude is compared to recent PPG amplitudes 46 of FIG. 6A in the same user, the average PPG pulse amplitude is substantially at or near its local maximum value. In this example, maximal MSKC pumping of the user consistently occurred during early diastole per the step timing markers 44 shown in FIG. 6C. Therefore, in this example, a local maximum average pulse amplitude may be a reasonable target PPG morphology for guiding a user to MCP, representing a relative preferred value of the measured characteristic (pulse amplitude, in this example) of the signal.

Various methods may be used, alone or in combination, to identify a target PPG signal characteristic that is indicative of optimal MSKC to CC relative timing. Quantifying metrics that target these characteristics, such as the PPG pulse amplitude as just described, can be used as part of a feedback loop to provide appropriate guidance to a user. Other examples of characteristics and metrics include beat-to-beat PPG waveform symmetry, peak and valley curvature, and/or signal complexity. The analysis may utilize the raw signal or a first or second derivative of the signals considered in the time domain, or can be considered in the frequency domain, wavelet space, or other domain. In all cases, the purpose is to utilize metrics that, alone or in combination, correlate to the timing relationship between the MSKC and the CC of the user. Details of such methods will be described more fully through the use of examples below.

As shown in FIGS. 6C and 6D, a PPG morphology of a user is sustained at substantially maximum average pulse amplitude 46, with FIG. 6D representing a shorter time interval for better visualization of waveform morphologies. An accompanying accelerometer signal 48 in relation to the ECG R-Wave timing indicated by 45 and the calculated maximal MSK pump (step) timing 49 are shown in FIGS. 6D and 6E. FIGS. 6B and 6E illustrate a PPG morphology of a user when the PPG waveform 47 approaches a local minimum in pulse amplitude, with FIG. 6E representing a shorter time interval. In exemplary systems, as the HR and MSKC frequency are increasingly different, the beat frequency caused by the overlapping waves increases and becomes less and less distinct and more and more difficult to identify clearly. For example, it may become difficult to measure a beat frequency of 60 beats per minute, running at a stride frequency of 180 steps per minute, when the HR is only 120 beats per minute, because the beats can become increasingly obscured as the beat frequency continues to rise. Therefore, in some embodiments, a separate MSKC sensor, such as an accelerometer, for identification of an MSKC signal, as described above, may optionally be utilized to identify the MSKC frequency of the user during rhythmic physical activity.

Figure 6F:
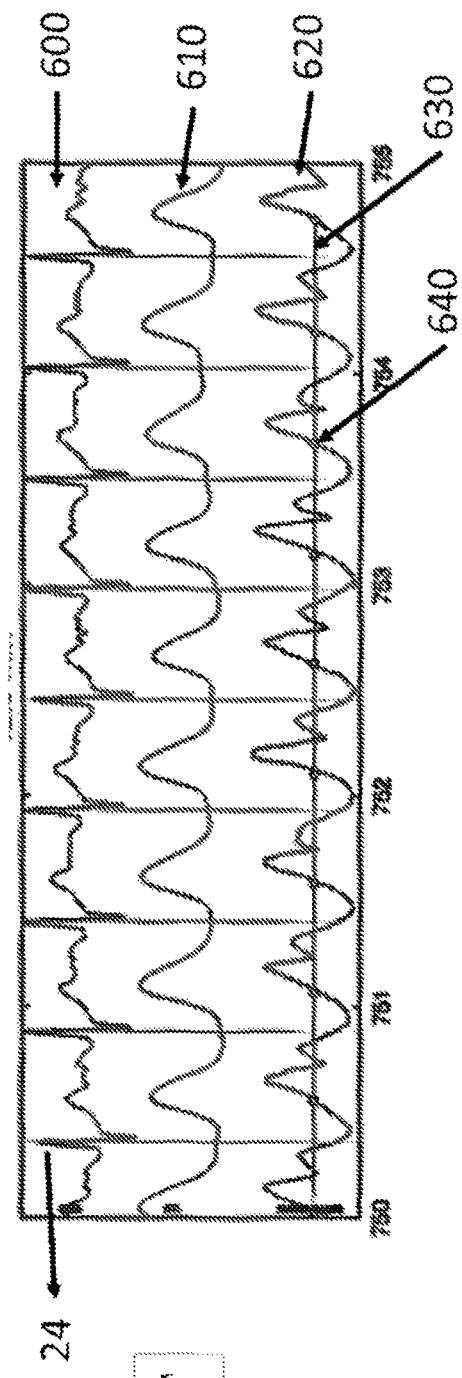

To further illustrate the behaviors described above, FIGS. 6F and 6G show plots of simultaneously collected ECG 600, PPG 610, and accelerometer 620 signals of a user walking on a treadmill. To generate these signals, a PPG sensor was placed on the user's forehead, while simultaneous ECG and accelerometer signals were obtained with respective sensors placed on the users chest. Horizontal line 630 represents the average accelerometer signal that is obtained when the user is not moving (i.e., approximately equivalent to 1 g, the acceleration due to gravity). As shown in FIG. 6F, the user's MSK pump timing (step timing), as indicated by the points 640, where the largest upslope during each MSKC of the accelerometer signal 620 crosses the horizontal line 630, occurs at approximately 40% of the RRI, using R-wave events 24 (FIG. 4B) as the timing marker for the CC. In this example of a relative MSKC to CC timing of 40% of the RRI, the PPG waveform 610 exhibits a morphology comprising a smooth rounded upper portion and a more-flattened lower portion, as shown in FIG. 6F.

Figure 6G:
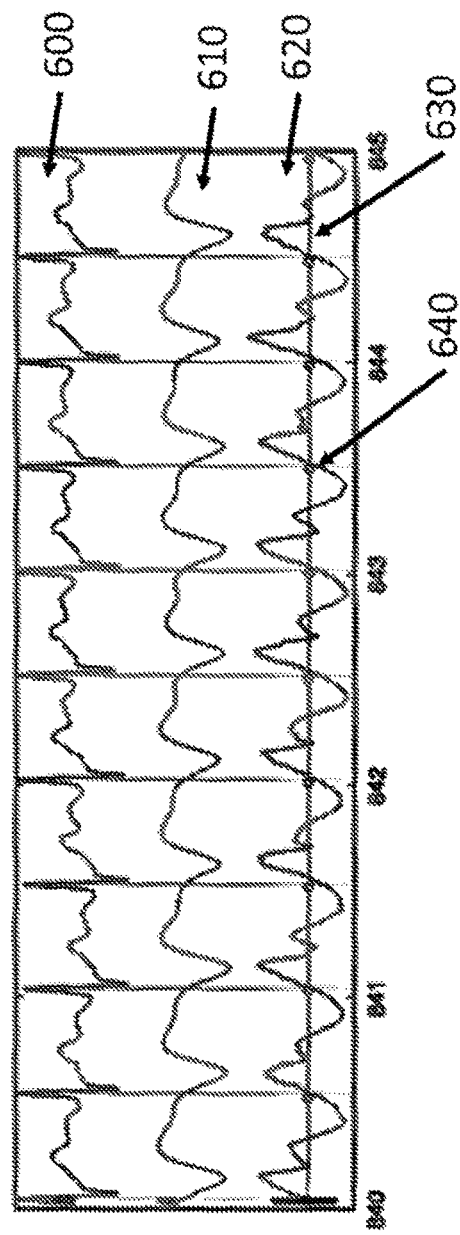

FIG. 6G illustrates changes in PPG signal 610 when the user steps at an MSKC to CC timing closer to 0% RRI. The waveform shape of signal 610 in FIG. 6G differs from the same signal in FIG. 6F, namely the upper portion is more flattened and the bottom is more rounded. Beyond the pulse amplitude as described above, these resulting morphologic differences in the PPG signals 610 in FIGS. 6F and 6G, seen also in FIGS. 6A-6E, may be used by the system to characterize the general degree of coordination between the MSKC and CC blood pumps, since the different waveform shapes correlate directly to the actual MSKC to CC timing relationship of the user. Such characterization of the morphology may be computed in a variety of ways, as will be described more fully below.

FIGS. 6G-F also represent signals from exemplary systems and methods that characterize an observed CC timing relationship with respect to an actual CC central blood pump timing of a user as a step in calculating a pulse transit time and/or assisting in calibration of the system for a specific user. For example, a PPG sensor at a specific peripheral location may be compared to a simultaneous ECG signal of the user in order to calibrate the system such that the true CC timing can be more accurately characterized with a PPG sensor alone after the user is no longer contacting both ECG leads.

As is illustrated in FIGS. 11 and 12, in some embodiments of the system and method, the pulse transit time of a sensed arterial pressure wave can be determined on a processor by comparing an aspect of a plethysmographic signal that repeats at the HR of the user (the CC timing signal of a plethysmogram) from a peripherally-mounted sensor (e.g., on the wrist or head of a user) to the timing of a simultaneous ECG signal. In example embodiments, as shown in FIG. 11, a PPG and/or IPG sensor 1110 in a device mounted on the wrist 1100 may be used simultaneously with an ECG sensor also in the same wrist-based system, with a first electrode continuously contacting the wrist of the user 1120, and a second electrode 1130 on an externally facing surface of the same device. The user may complete the ECG circuit 140 by touching a finger of their opposite hand to the second electrode 1130 of the sensor, so that the ECG signal may be measured and an ECG CC timing determined on a processor, for comparison to the simultaneously measured plethysmographic CC signal timing, on the same processor or a different processor.

Alternatively, in another exemplary embodiment as shown in FIG. 12, an ear-based device 1200 may include one or more sensors of blood pressure, volume or flow 1210 (e.g. plethysmographic) as well as a pair of electrodes, one in contact with the skin of the head or ear of the user 1220, and the other insulated from the tissue of the head or ear, but accessible to the touch of the user's hand 1230, as shown in FIG. 12. In such exemplary embodiments, the user may touch the exposed electrode 1230 with the skin of a finger, as shown in FIG. 12, for example a finger of the user's left hand when touching a head-based device, in order to complete the ECG circuit 1240 and measure the ECG and PPG signals simultaneously for comparison of their CC signals of CC timing.

Figure 7A:
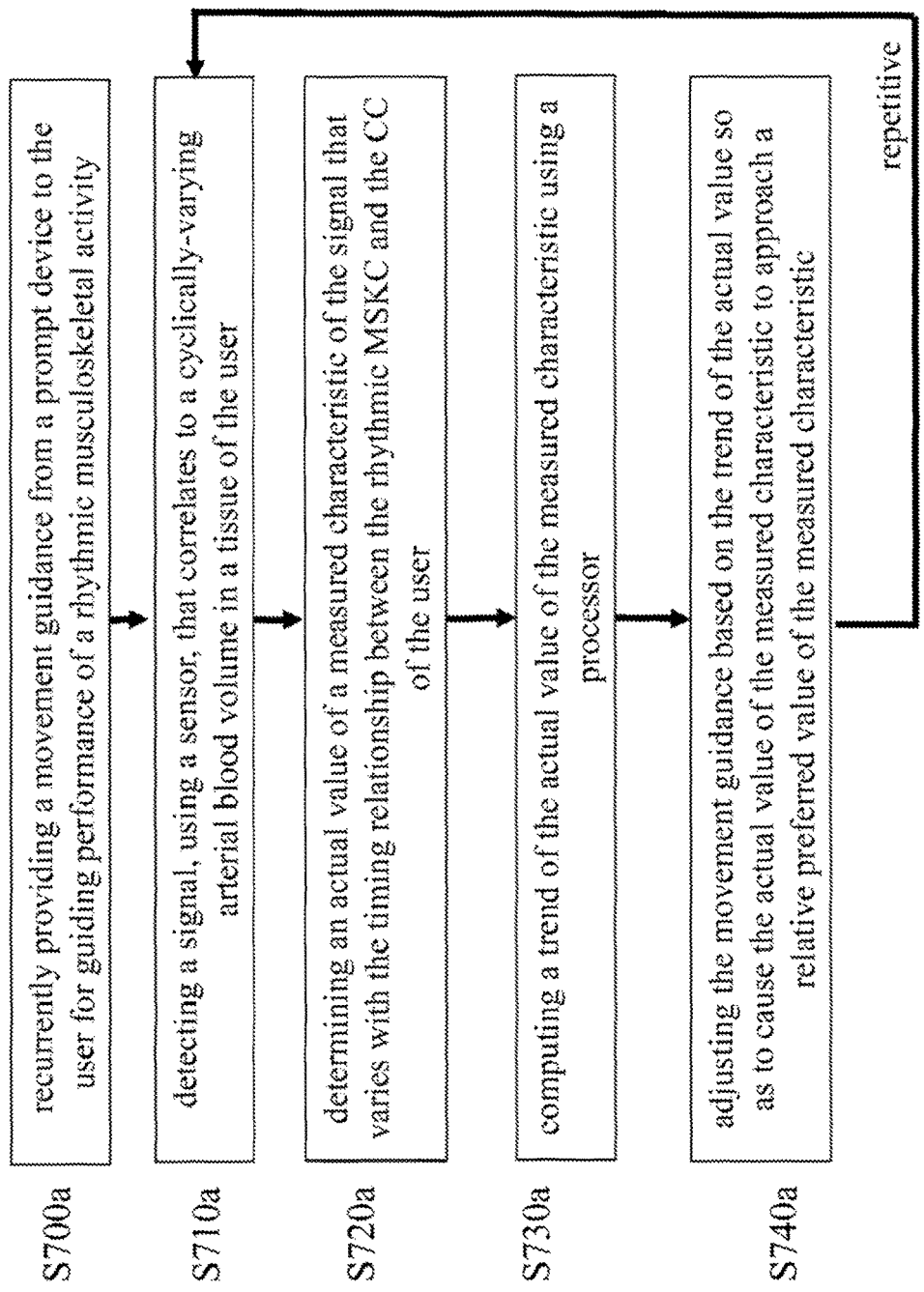
FIGS. 7A-B illustrate flow charts for synchronizing a timing of a rhythmic MSKC with a timing of a CC of a user using a measure of arterial blood pressure, volume, or flow (e.g. plethysmography), in accordance with preferred embodiments.

FIG. 7A illustrates a flow chart for favorably coordinating a timing relationship between an MSKC of a rhythmic musculoskeletal activity of a user and a CC of the user using a sensor to provide signals that correlate to a cyclically-varying arterial blood volume in a tissue of the user, for example, a plethysmography sensor. As shown in FIG. 7A, a preferred method of favorably coordinating a timing relationship between an MSKC of a rhythmic musculoskeletal activity of a user and a CC of the user includes the steps of recurrently providing a movement guidance from a prompt device to the user for guiding performance of the rhythmic musculoskeletal activity S700a; detecting a signal, using a sensor, that correlates to a cyclically-varying arterial blood volume in a tissue of the user S710a; determining an actual value of a measured characteristic of the signal that varies with the timing relationship between the MSKC and the CC of the user S720a; computing a trend of the actual value of the measured characteristic using a processor S730a; and adjusting the movement guidance based on the trend of the actual value of the measured characteristic so as to cause the actual value of the measured characteristic to approach a relative preferred value of the measured characteristic S740a. This process continues by returning after step S740a to step S710a in a repetitive manner, for example, repeating for a duration of an exercise, or as long as certain exercise or physiological data are maintained, or for a predetermined period of time.

Figure 7B:
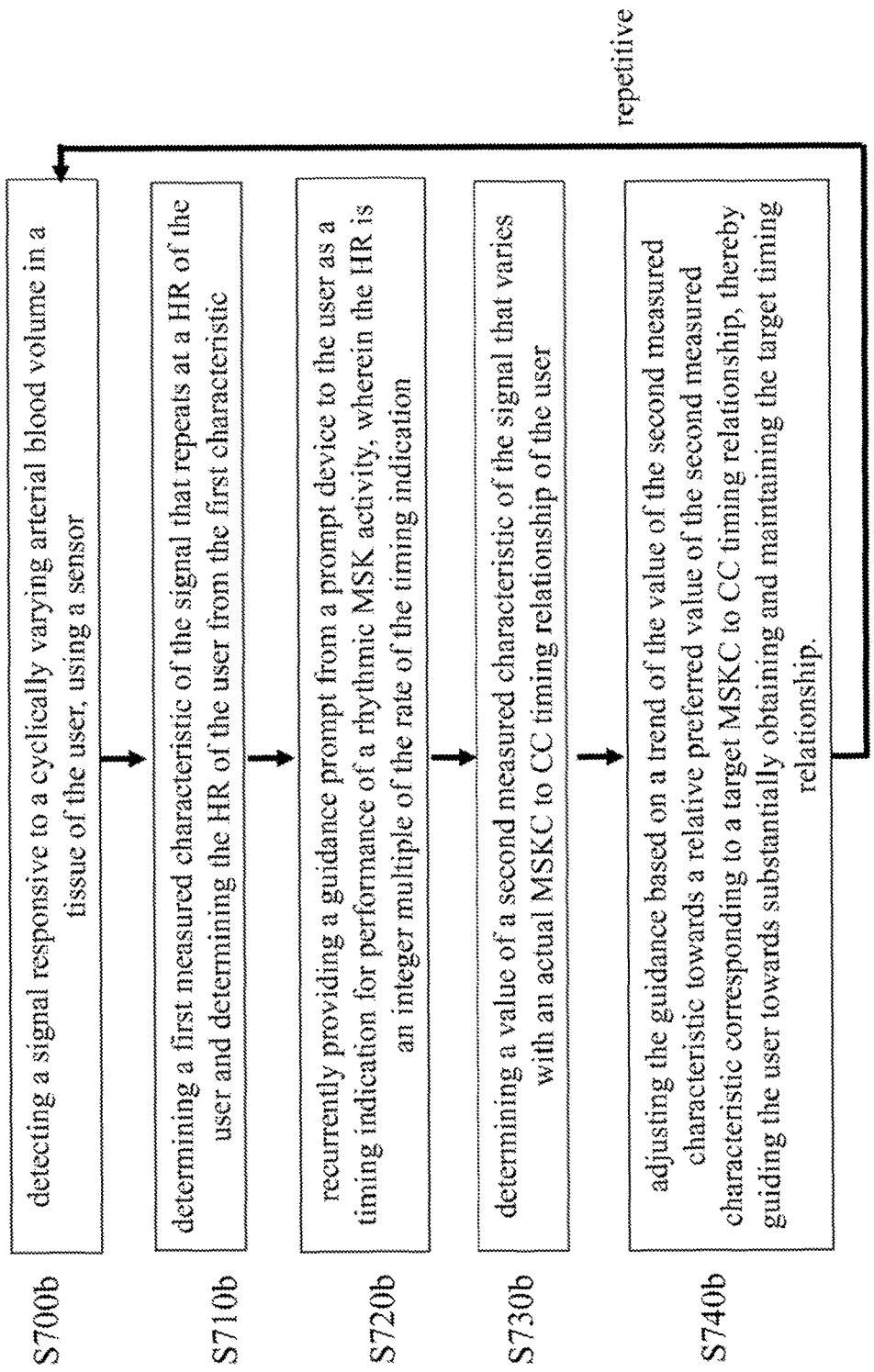

In some embodiments, the methods of FIGS. 7A-B may include a calibration process. The calibration process may include the steps of detecting a second characteristic of the signal or one or more additional signals corresponding to a physiological metric that varies with the timing relationship between the MSKC and the CC of the user, using the sensor or one or more additional sensors, and determining the relative preferred value of the measured characteristic as a relative value of the trend that corresponds with a preferred value of the physiological metric. Further examples of such calibration processes are provided below in the section titled Calibration Methods. In exemplary embodiments, the movement guidance comprises an audible, visual, or tactile prompt. In example implementations, the movement guidance prompts the user in at least one of MSK activity timing and MSK activity effort. For example, activity timing guidance may provide the prompt to the user at a prompt rate, such that the HR of the user is substantially an integer multiple of the prompt rate, and adjusting the movement guidance means adjusting the prompt rate. In other exemplary embodiments, adjusting the movement guidance means guiding the user to alter a stride length during running or walking; to change a gear while riding a bicycle; to change a distance of movement, resistance, or incline using exercise equipment; or to modify a stroke length during rowing or swimming, in each case in order to modify their effort at a given MSKC frequency.

In certain embodiments, the relative preferred value is a target behavior of the trend of the value of the measured characteristic and further adjusting the guidance based on a difference between trend of the actual value and the relative preferred value of the measured characteristic guides the user towards substantially obtaining and maintaining the relative preferred value ("target behavior") of the measured characteristic. For example, a target behavior of the trend of the value of the measured characteristic of a PPG waveform may include preferred behaviors such as, for example, at least one of an increasing pulse amplitude, a decreasing waveform complexity, and a change in timing of an aspect of the PPG signal that repeats at a HR of the user towards a target timing relationship relative to an aspect of an MSKC timing signal that repeats at an MSKR of the user.

In additional embodiments of the method, the relative preferred value may be a target value of the measured characteristic, said target value corresponding to the target timing relationship between the MSKC and the CC of the user. For example, a target value of a PPG waveform may include exemplary preferred relative values such as at least one of local maximum pulse amplitude, a local minimum waveform complexity, and a target timing relationship of an aspect of the PPG signal that repeats at a HR of the user relative to an aspect of an MSKC timing signal that repeats at an MSKR of the user. FIG. 7B illustrates another flow chart for favorably coordinating a timing of a rhythmic MSKC with a timing of a CC of a user using a sensor that provides signals that correlate to the cyclically-varying arterial blood volume in a tissue of the user, such as, for example, a plethysmography sensor (e.g. PPG or IPG), in accordance with a preferred embodiment. Exemplary steps include the repetitive cycle of detecting a signal, using a sensor, responsive to cyclically varying blood volume in a tissue of the user S700b; determining a first measured characteristic of the signal that repeats at a HR of the user and determining the HR of the user from the first characteristic S710b; recurrently providing a guidance prompt from a prompt device to the user as a timing indication for performance of a rhythmic MSK activity, wherein the HR is an integer multiple of the rate of the timing indication 720b; determining a value of a second measured characteristic of the signal that varies with an actual MSKC to CC timing relationship of the user 730b; and adjusting the guidance based on a trend of the value of the second measured characteristic towards a relative preferred value of the second measured characteristic corresponding to a target MSKC to CC timing relationship, thereby guiding the user towards substantially obtaining and maintaining the target timing relationship 740b. After completion of step S740b, the process loops back to S700b, making the process repetitive, repeating, for example, for a duration of an exercise or a predetermined period of time.

In an exemplary embodiment, the detected signal S700b may comprise a PPG signal, and the first measured characteristic that repeats at the HR of the user 710b may be the peaks of the signal that correspond with systolic arterial pressure 31 (FIG. 6E). In certain exemplary embodiments wherein the detected signal S700b is a PPG signal, the first measured characteristic 710b may be available to correlate to the HR of a user only intermittently, but for adequate durations to calculate a HR of a user. For example, referring to the beat phenomenon illustrated in FIG. 6A, the first measured characteristic 710b may be the regularly occurring peaks of the signal that equal or surpass a predefined or relative amplitude or shape characteristic (such as seen in FIG. 6D, 46), because, for example, the larger and/or sharper systolic peaks in the PPG may be easier to identify reliably. An exemplary signal with intermittently oscillating PPG amplitudes is illustrated in FIG. 6A, wherein the relatively larger and easier to identify systolic peaks 31, magnified in FIG. 6D, may be more accessible for reliable interpretation than the relatively smaller and potentially more difficult to identify systolic peaks 31 in FIG. 6E.

Alternative embodiments of the method of FIG. 7B may alternatively or additionally leverage a measured characteristic that is different from the first measured characteristic described in step S710b in order to determine the HR of the user. For example, if the value of the MSKR is available from another sensor (e.g. accelerometer), then the frequency of the beat phenomenon, as illustrated in FIG. 6A, may be measured from the PPG signal and then added to or subtracted from the value of the MSKR in order to obtain the value of the HR. In further embodiments, CC timing measurements, for example using plethysmography or electrocardiography, can be improved by measuring signals sensitive to the MSKC, such as through the use of an accelerometer, and incorporating these signal values into a noise cancellation or attenuation methodology. In further exemplary implementations of FIG. 7B, adjusting the guidance means adjusting the prompt rate. In yet other exemplary embodiments, adjusting the guidance includes guiding the user to alter effort at a given MSKC frequency (e.g. alter stride or stroke length at a given MSKC cadence, incline or resistance on an exercise device, etc.).

Referring now to the flowcharts shown in FIGS. 7A and 7B, in some embodiments, the measured characteristic S720a and second measured characteristic S730b may include a pulse amplitude of a plethysmography signal detected in S710a and S700b, respectively, as is illustrated by the exemplary PPG signal in FIG. 6 and as was described above. Alternatively or additionally, in some embodiments, the measured characteristics S720a and S730b may include a measure of the complexity of the signal from the sensor. The amount of smoothness or "noise" in a waveform relates to the complexity of the signal. For example, in certain circumstances, when the CC and MSKC contributions to blood volume in the local tissue at the measurement site are cycling with each other constructively, the pulse amplitude is greatest, as shown by waveform 46 in FIGS. 6A and 6D, and the waveform is generally smooth or substantially sinusoidal, resulting in reduced complexity. Conversely, when the CC and MSKC contributions are out of alignment, there is an appearance of extra features in the waveform (over the timing of one complete CC) resulting in increased complexity, such as seen by 47 in FIG. 6E.

In further embodiments, the asymmetry of the sensed signal waveforms may be analyzed with a processor in order to determine additional timing information, for example, to determine whether the MSK timing is occurring slightly early relative to a target timing relationship or slightly late relative to a target timing relationship. Additionally or alternatively, the measured characteristic of the signal may be computed using a combination of two or more unique characteristics of the signal that vary with the timing relationship between the MSKC and the CC of the user. For example, at least one of the trends in changes of aspects of the complexity, amplitude, and symmetry of the PPG signal may be identified and utilized simultaneously in the steps of determining a value of a second measured characteristic S730b, as described in FIG. 7B, or in computing a trend of the actual value of the measured characteristic on a processor S730a, as described in FIG. 7B. In one such embodiment, target characteristics of a PPG signal on the head of a user may include a target combination of both maximal relative pulse amplitude plus minimal signal complexity. In other embodiments, the measured characteristic may include the relative phase between the two contributing signals as computed, for example, using a Fourier transform and retaining the complex term (phase). In yet another example embodiment, the characteristic may be a measure of the number of inflection points of the waveform per cycle of the MSKC or CC. As noted above with respect to waveforms 610 in FIGS. 6F-G, another measured characteristic that may be considered alone or in combination may include the relative curvature of the PPG peaks and valleys, quantified for example by computing a ratio of the relative amount of change in signal amplitude adjacent to the peak signal to the amount of change adjacent to the valley, considered over individual cycles in the PPG.

Steps 730a and 730b include determining an actual value of the measured characteristic of the signal that varies with the timing relationship between the MSKC to CC of the user. The trend may be computed as the difference in the value observed, or a series of values observed, at two or more different times, such as the most recently observed value and the value available immediately preceding it, or alternatively, the average change over several recent sample periods. Considering the PPG signal 41 of FIG. 6A, the trend of the pulse amplitude can be seen to oscillate approximately seven times over the duration of the graph. In the final seconds of the graph in FIG. 6A, the most recent trend exhibits the behavior of a decreasing pulse amplitude, and a decreasing average pulse amplitude. Steps S740a and S740b include a relative preferred value of the measured characteristic corresponding to a target relative MSKC to CC timing. The term "relative preferred value" used in conjunction with FIG. 7 refers to a preferred value of the measured characteristic in comparison to the value of recent instances of the characteristic, or equivalently, a preferred relationship of the actual value of the measured characteristic relative to the trend of the value of the measured characteristic, as is described more fully below. This preferred relationship may correlate with an MSKC to CC timing relationship consistent with MCP.

In some embodiments, the target MSKC to CC timing may target the condition of MCP. The value of the measured characteristic corresponding to this condition may depend on the nature of the signals detected in S710a and S700b and where on the body the sensor is located. In one embodiment, the relative preferred value of the measured characteristic during MCP may correspond to a pulse amplitude of an observed plethysmography signal exhibiting a behavior of reaching its local instantaneous maximum in its trend over the recent history of the observed pulse amplitude. Alternatively, the relative preferred value may correspond to a local maximum in the average of the pulse amplitude compared to its recent history. In other embodiments, a local minimum in the trend of the pulse amplitude may be associated with MCP, or an average maximum pulse amplitude minus the average minimum pulse amplitude over a given rolling window of time. Similarly, in yet another embodiment, the relative preferred value may correspond to a local minimum complexity in the PPG signal. Alternatively, the relative preferred value may correspond to a local maximum complexity in comparison to its recent history. In further exemplary embodiments, the relative preferred value may correspond to a maximal local average of the absolute values of the derivative of the PPG signal or to a minimal local average of the absolute values of the second derivatives of the PPG signal. In other embodiments, the trend of the measured characteristic may be used to identify a specific relative value of the measured characteristic corresponding, for example, to the value of a local maximum or, in another example, a value of a local minimum in the trend. The system may then adjust the guidance based on a difference between the actual value of the measured characteristic and this previously identified specific relative value from the trend. In another example embodiment, the relative value of the measured characteristic may correspond to a point in the trend when the value changes sign from negative to positive, or in a different example, from positive to negative, crossing a threshold value of zero either in a positive slope of the trend or a negative slope in the trend, respectively. In some embodiments, the relative preferred value corresponding to a target MSKC to CC timing is determined empirically according to a calibration process, which is described more fully below.

In an exemplary system, the user is provided with a guidance prompt comprising a metronome that repeats at a rate that matches an expected HR of the user during their rhythmic activity. The user times their rhythmic activity to occur with the metronome, and as the user's HR approaches this rate, a PPG signal measured on the user, such as in FIG. 6A, begins to exhibit a behavior of a cycling pulse amplitude (pulse amplitude representing the measured characteristic of the signal). Considering a relative preferred value of the measured characteristic to correspond to a local maximum in the pulse amplitude, the system may increase the period of the metronome when the trend of actual value of the measured pulse amplitude stops increasing over time and begins to decrease. If the trend of the pulse amplitude responds to the change in metronome by increasing, the metronome period continues unchanged. When the pulse amplitude again begins to decrease, having passed its local maximum, the system decreases the metronome period so as to reverse the trend in the decreasing pulse amplitude, thereby causing the pulse amplitude to approach the relative preferred value and substantially maintain the target timing relationship between the user's MSKC and CC.

In addition to the steps illustrated in FIGS. 7A and 7B, in order to obtain an MSKR, embodiments may include a second signal from a second sensor responsive to the MSKC of the user, for example, an accelerometer signal 48 from an accelerometer, as shown in FIGS. 6D and 6E, may be used.

In certain embodiments, one of the characteristics of the signal that correlates to a cyclically varying arterial blood volume in a tissue of the user may be a timing of a recurrent aspect of the signal that varies with the HR of the user, which may be used alone or in combination with exemplary measured characteristics of the signal previously described. For example, relatively high pulse amplitude may be one preferred measured characteristic of a PPG signal in a tissue on the head of a user indicating that the MSKC to CC timing relationship is approaching a preferred MSKC to CC timing relationship. In this example, pulse peak timing at the higher pulse amplitude may be an aspect of the signal that correlates with a CC timing, such that the timing of the CC can thereby be compared to the timing of the MSKC detected from a second sensor (e.g. accelerometer), and these signal timings can be used to determine both a measured and an actual MSKC to CC timing relationship using a processor, wherein, for example, the actual timing relationship is corrected for pulse transit time. The timing indication of the prompt may then be adjusted, as indicated, based on a difference between the actual timing relationship and the preferred timing relationship, so as to reduce the magnitude of the difference.

In some embodiments, the method of FIGS. 7A and 7B may further include providing MSK activity guidance or adjusting MSK activity guidance only when the absolute value of a difference between the musculoskeletal activity cycle rate (MSKR) and HR is less than, or less than or equal to, the specified allowable difference.

Figure 8:
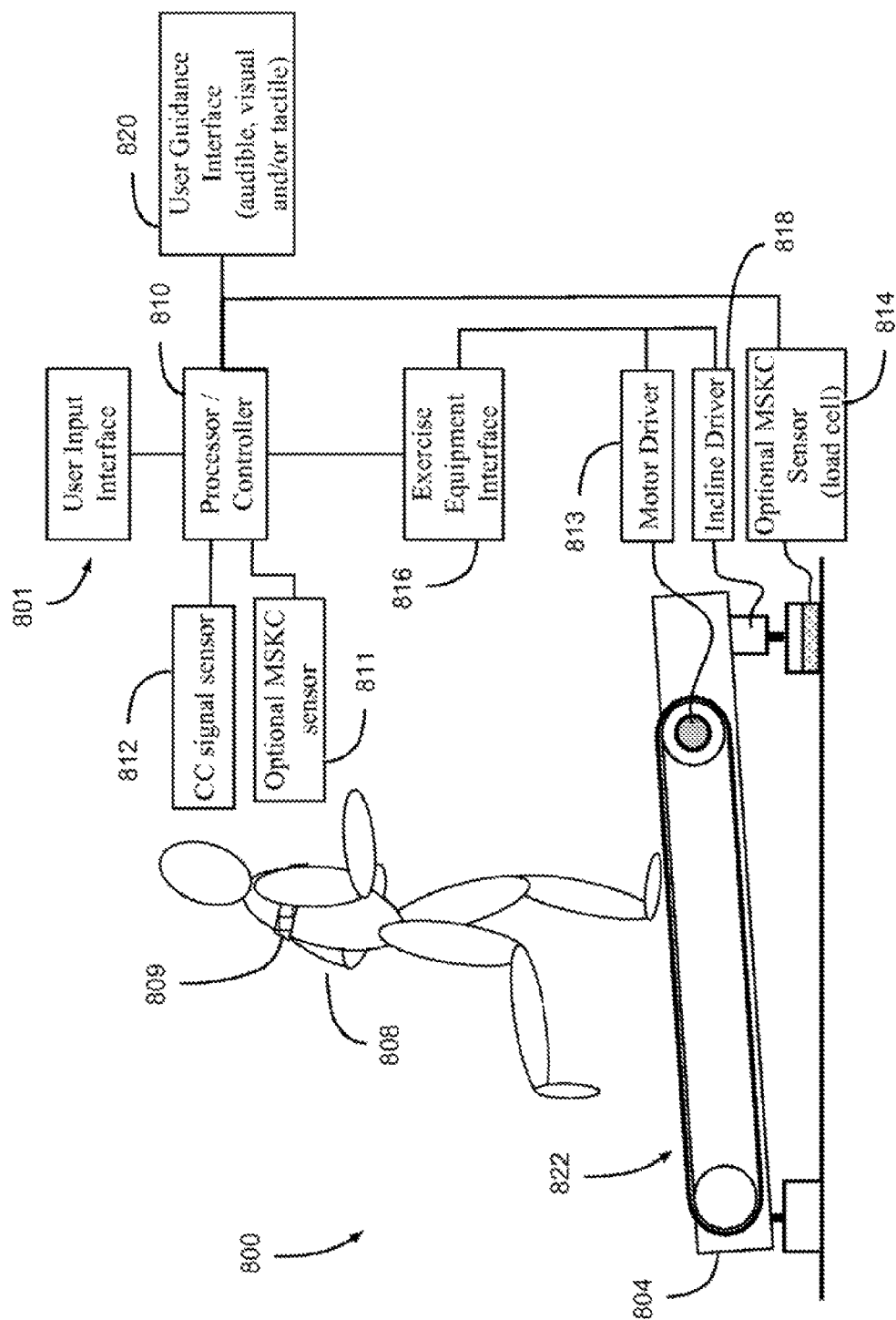
FIG. 8 illustrates a treadmill system for sensing a CC and MSKC timing of a user and guiding a user to the target MSKC to CC timing relationship, in accordance with a preferred embodiment.

Exercise Systems and/or Technologies for Favorably Coordinating CC and MSKC Timing Now turning to exemplary exercise equipment systems for implementing systems and methods of FIGS. 1-7. FIG. 8 illustrates a treadmill system for sensing a CC and MSKC timing of a user and guiding a user to the target MSKC to CC timing relationship, in accordance with a preferred embodiment. A treadmill system, as shown in FIG. 8, may be used to determine a target MSKC to CC timing relationship, as well as to guide a user to the target MSKC to CC timing relationship. As shown in FIG. 8, the treadmill system 800 may include a user input interface 801, a processor/controller 810, an exercise equipment interface 816, a user guidance interface 820, a motor driver 813, an incline driver 818, and a track 822 on which the user 808 may run or walk. The treadmill system 800 may include a chest strap 809 for measuring the CC of the user 808 with CC sensor 812. Alternatively, any type of wearable sensor or device may be worn by the user to measure a CC of the user, for example a smart watch and/or a chest strap 809 with HR and/or MSKC sensor. The MSKC of the user may be measured in one embodiment by using sensor 811 included, for example, within chest strap 809, or in another embodiment as a component of the treadmill such as load cell 814 or an accelerometer. In yet another embodiment, a single sensor, combining the function of sensors 811 and 812, may be used for sensing both the CC and MSKC of the user or, for example a PPG sensor, as was described more fully above. The functioning and embodiments of the user input interface 801, CC signal sensor 812, MSKC sensor 811 or 814, processor 810, and exercise equipment interface 816 were described above in connection with FIGS. 1 and 2.

As shown in FIG. 8, an MSKC sensor 814, for example a load sensor, may be used to sense the load of the user 808 as a foot of the user strikes the track 822 of the treadmill 804. In some embodiments, the information collected by the MSKC sensor and CC sensor may be transmitted to the processor for determining the actual and target MSKC to CC timing relationships, as described above. Sensor 814 represents one example of a location and type of MSKC sensor that can be used with the exercise equipment. In addition to the body-worn MSKC sensors described previously, other examples of MSKC sensors on the equipment include vibration, switch, optical, video, and pressure sensors, or any others well known in the exercise equipment industry. In further embodiments, a computer, for example, a tablet computer, may be placed on or attached to the exercise equipment, said computer including or communicating with at least one of an MSKC sensor (e.g. accelerometer or user facing camera) and a CC sensor (e.g. user facing camera).

Also as shown in FIG. 8, an exercise equipment interface 816, user input interface 801, or user guidance interface 820 may be used by a user or automatically controlled by the processor 810 to adjust the motor driver 813 to increase or decrease speed and the incline driver 818 to raise or lower the incline of track 822. Further, additional sensors may be used to detect hand gestures or other body movements that are recognized as commands for adjusting the treadmill incline, treadmill speed, type of music, playlist selection, volume control, type of graphical display, graphical display selection, or any other type of controls. In some embodiments, one or more automation features may be used to guide a user towards a target MSKC to CC timing relationship, for example using the user guidance interface 820. Alternatively, a user may abort an automatic setting or turn off an automatic setting to enable manual control of the motor driver 813 and incline driver 818 or any other feature of the treadmill.

In some embodiments, exercise equipment interface 816, user input interface 801, or user guidance interface 820 may also provide visual displays of information, such as raw data, processed data, or a combination thereof. For example, a HR, ECG, EEG, estimations of fat or sugar metabolism, blood insulin concentration, blood glucose concentration, step rate, MCP of the arms and/or legs, tissue lactate concentration, watts per beat, meters per beat, distance, and heel strike of a user may be displayed on the interface 801, 816, 820. In some embodiments, user guidance interface 820 may be used to provide guidance to the user. Guidance may be provided in an audible cue, visual display, tactile feedback, or other features that alert the user to a change in guidance, for example to increase or decrease stride length; to guide the user towards stepping every 2 beats, 3 beats, or 4 beats; or to coach the user to improve MSKC timing, concentration, or effort. As described above, reaching a target MSKC to CC timing relationship and other desired physical states, including desired HRs and MSK activity levels may be accomplished with treadmill system 800.

Figure 9:
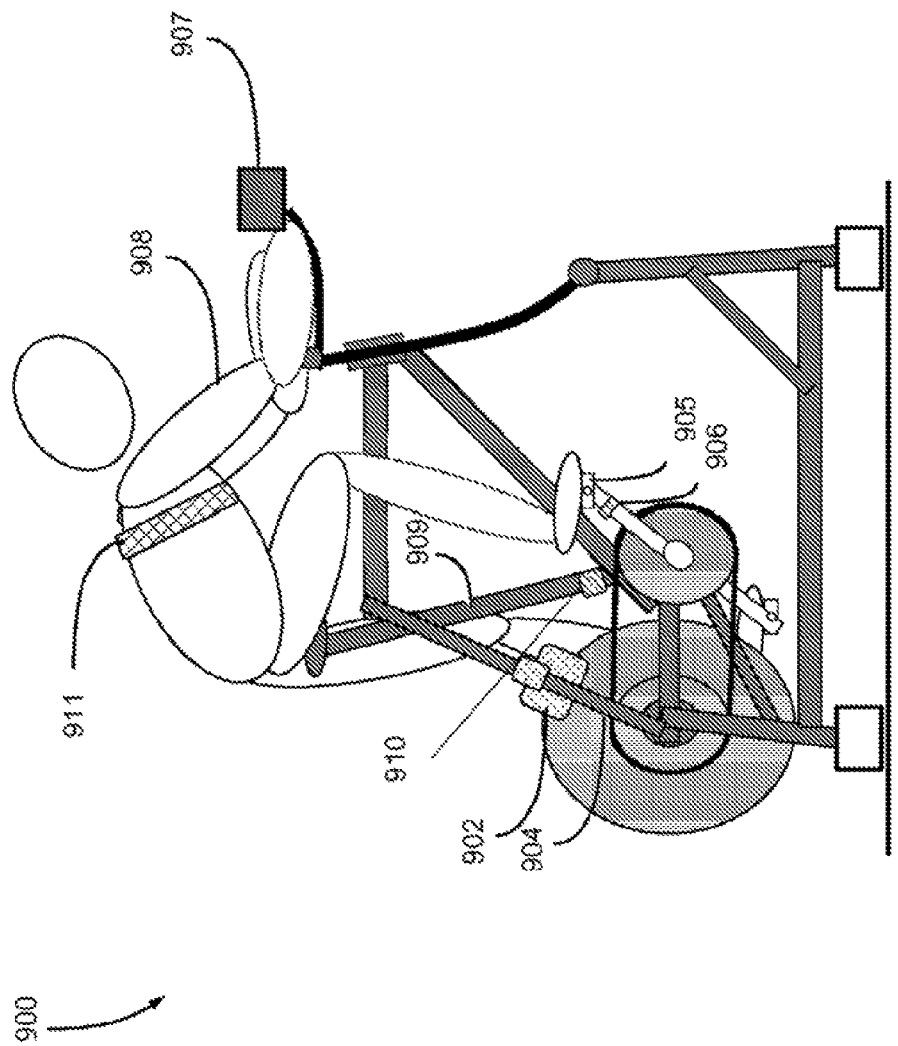
FIG. 9 illustrates a biking system for sensing a CC and MSKC timing of a user and guiding a user to the target MSKC to CC timing relationship, in accordance with an alternative preferred embodiment.

FIG. 9 illustrates a biking system 900 including an exercise equipment interface, user input interface, or user guidance interface 907 for sensing a CC and MSKC timing of a user 908 and guiding the user to a target MSKC to CC timing relationship, in accordance with an alternative preferred embodiment. As show in FIG. 9, one or more sensors may be integrated with one or more components of a bike, such as a pedal, tire, crank, hub, spoke, derailleur, or bike chain to obtain measurements of speed, distance, acceleration, power, etc., and to determine relationships with other physiological metrics. As shown in FIG. 9, a stationary bike may include a sensor 902 on the back frame tube 904, a sensor 910 on a second frame tube 909, a sensor on the pedal 905, a first foot sensor on the first pedal crank 906, and a second foot sensor (not shown) on the second pedal crank. One or more of the bike sensors as described above may be used to identify an actual or a preferred MSKC timing. For example, each revolution of the pedal may equal one MSKC, or may equal two, including one MSKC for each leg. In some embodiments, the signals from the one or more MSKC sensors on the bike may be compared to the timing of signals from at least one sensor worn by the user, for example a chest strap sensor 911 to sense a CC of the user 908. Comparison of a body worn ECG based CC sensor to an exercise equipment based CC sensor may be useful in calibration of embodiments of the system. Alternatively, a chest patch sensor, an implanted sensor, a wrist-based sensor, a head-based sensor, or another device previously described above may be worn by the user to measure a CC and/or MSKC of the user. Thus, for example, body versus pedal MSKC timing information may be determined and synchronized according to embodiments of exercise equipment as described herein. In some embodiments, synchronizing body versus pedal MSKC timing may require a characterization step, as will be described below. Alternatively, a sensed body movement metric may be determined and synchronized in order to calibrate the system MSKC pump timing. In some embodiments, synchronization or characterization of clocks on sensors, may be done using one or more accelerometers. Synchronization and characterization may require the user to perform coordinated actions that register distinguishable events in the data provided by the sensors, such that the distinguishable events may be used for correlating internal clocks of the sensors.

For a non-stationary or stationary bike, as shown in FIG. 9, exemplary embodiments of characterization algorithms include use of a body versus body MSKC sensor timing comparison. Further embodiments include a body MSKC sensor versus bike MSKC sensor timing comparison, each having an internal clock. In some embodiments, syncing the two clocks intermittently may be performed to characterize or check characterization at periodic events such as on the occasion that the user stands up on the pedals during MSKC. For example, this characterization maneuver may be a required step every few minutes during the use of the system. The characterization maneuver may incorporate two identical chip and accelerometer configurations (e.g. chest strap and bike crank) to correct for clock drift.

Calibration Methods

Figure 10:
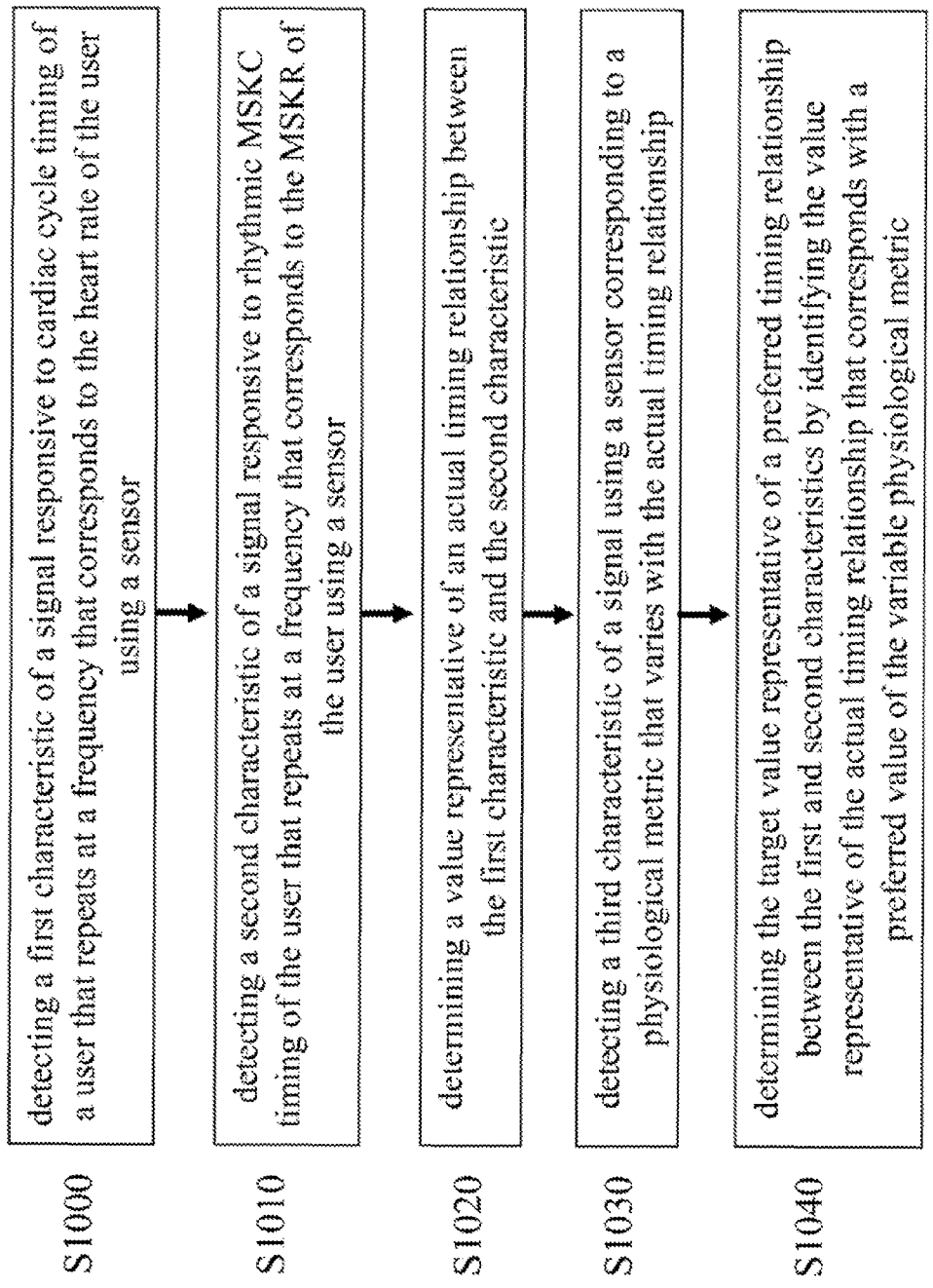
FIG. 10 illustrates a flow chart for calibrating a system for determining a target MSKC to CC timing relationship, in accordance with a preferred embodiment.

FIG. 10 illustrates a flow chart for determining a target MSKC to CC timing relationship empirically, i.e., "calibrating" a system, in accordance with a preferred embodiment. As shown in FIG. 10, a method for determining a target MSKC to CC timing relationship of a preferred embodiment includes detecting a first characteristic of a signal responsive to a CC timing of a user that repeats at a frequency that corresponds to the HR of the user using a sensor S1000; detecting a second characteristic of a signal responsive to a rhythmic MSK activity timing of the user that repeats at a frequency that corresponds to the MSKR of the user using a sensor S1010; determining a value representative of an actual timing relationship between the first characteristic and the second characteristic S1020; detecting a third characteristic of a signal using a sensor corresponding to a physiological metric that varies with the actual timing relationship S1030; and determining the target value representative of a preferred timing relationship between the first and second characteristics by identifying the value representative of the actual timing relationship that corresponds with a preferred value of the variable physiological metric S1040.

The method preferably functions to calibrate or recalibrate the system empirically so that the system may be tailored to each user, activity, device configuration, and/or time. For example, the relationship between MSKC timing and CC timing that leads to a preferred value of a physiologic variable may vary among users engaged in a similar physical activity, between different activities for one user, and/or between different instances of the same activity over time. Additionally, the specific system configuration can affect the measured relative timing. For example, use of the ECG T-wave vs. the R-wave vs. the peak systolic amplitude of a PPG signal as a timing indication impacts the measured CC timing, as does the location of the PPG sensor. Additionally, the location of a crank sensor placed on a bicycle and the location of the MSKC sensor incorporated within a treadmill system impacts the values and timing of the signals used to measure MSKC timing independent of the underlying timing of the CC and MSKC blood pumps. Thus, the method as shown in FIG. 10 functions to calibrate or recalibrate the system empirically to correct for or plan for any of the factors that can affect the measured MSKC to CC timing relationship and its relationship to a target physiological condition (e.g., MCP) or a preferred value of a physiologic variable (e.g., a reduced HR).

In some embodiments, a system may be configured to determine the optimal relative MSKC to CC timing of a user once. Alternatively, the system may temporarily switch back to a "calibration mode" periodically to ensure ongoing optimization of timing. In both cases, in an example embodiment, a HR of a user while exercising at a given work load may correlate with the timing of the MSKC relative to that of the CC, with relatively lower HR values at a given work load associated with improved overall blood pump hemodynamics. By exposing the user to a variety of relative MSKC to CC timing values over a period of time, and then identifying the relative timing value, characteristic, or relative value relationship associated with the lowest HR, the system may be used to identify the "favorable" or "optimal" timing relationship and/or hemodynamic sensor signal characteristics for the specific user, activity, and system configuration in use during the calibration process. This empirically determined value, signal characteristic, or relative value relationship may then be used subsequently to represent the target MSKC to CC timing relationship. Optimal timing relationships may also be derived from additional or alternative measures other than HR.

As shown in FIG. 10, step S1000 includes detecting, using a sensor, a first characteristic of a signal responsive to a CC timing of a user that repeats at a frequency that corresponds to the HR of the user. Step S1000 may, in example embodiments, function to identify a recurrent aspect of a CC of the user, as described above. In some embodiments, the first characteristic may be one aspect of a signal, for example from ECG or PPG, such that other aspects may be used to define other characteristics, for example an MSKR.

As shown in FIG. 10, step S1010 includes detecting a second characteristic of a signal responsive to rhythmic MSKC timing of the user that repeats at a frequency that corresponds to the MSKR of the user using a sensor. Step S1010 may, in example embodiments, function to determine a recurrent aspect of an MSKC of a user, as described above. In some embodiments, the sensor in S1000 and S1010 may be the same sensor, for example a PPG sensor. Alternatively, the sensors in S1000 and S1010 may include distinct sensors, for example an ECG and an accelerometer or a PPG and an accelerometer. In some embodiments, the first characteristic and the second characteristic are the same aspect of a first signal from a first sensor. Alternatively, the first characteristic and the second characteristic may be different aspects of a first signal from the first sensor. For example, one or more features of a PPG signal may be used to determine a CC and MSKC timing or timing relationship of a user, as described above in accordance with FIGS. 6 and 7. In some embodiments, the first characteristic and second characteristic may be derived from independent first and second signals from first and second sensors, respectively.

As shown in FIG. 10, step S1020 includes determining a value representative of an actual timing relationship between the first characteristic and the second characteristic. Step 1020 may function to determine a timing relationship between a CC and MSKC of a user using the observed individual timings of the first and second characteristics of steps S1000 and S1010, respectively. In alternative embodiments, the actual timing relationship may be determined by using a cross correlation between the first characteristic and the second characteristic.

As shown in FIG. 10, step S1030 includes detecting a third characteristic using a sensor corresponding to a physiological metric that varies with the actual timing relationship. Step S1030 preferably functions to further measure a third physiological parameter of a user as compared to the first and second characteristics. Example physiologic metrics include, but are not limited to the user's HR, systolic and/or diastolic blood pressure, cardiac output, cardiac perfusion, muscle perfusion, muscle pH, cerebral perfusion, EEG activity, respiratory gases (e.g., VO2, VCO2, RER), tissue or blood glucose and lactate levels, and blood insulin levels. In each case, the corresponding preferred value of the metric reflects a desired condition, generally associated with a relatively improved physiologic economy, typically an appropriate minimum or maximum of the respective measure of interest.

Further, the sensors in S1000, S1010, and S1030 may be the same sensor in certain embodiments, or can use two or more different sensors in other embodiments, for example S1000 may be an ECG, while S1010 may be an accelerometer, while S1030 may be a metabolic measurement system for calculating oxygen consumption, $CO_2$ production, respiratory volumes, and other related measurements. In an alternative embodiment, the sensor of S1010, S1010, and S1030 can all represent one or more PPG sensors.

In some embodiments, the system may guide the user towards a target or preferred value of a physiological metric, such that the physiological metric is at a beneficial or advantageous level to the user. Additionally, the third characteristic may be used to determine when a user achieves MCP or a target MSKC to CC timing relationship. In some embodiments, the first characteristic and the third characteristic may be the same aspect of a first signal from a first or third sensor. Alternatively, the first characteristic and the third characteristic may be different aspects of a first signal from the first or third sensor. Alternatively, the first, second, and third characteristics may be three distinct aspects of a first signal from the first sensor. In some embodiments, the first, second or third characteristics may include a Fourier transform.

As shown in FIG. 10, step S1040 includes determining the target value representative of a preferred timing relationship between the first and second characteristics by identifying the value representative of the actual timing relationship between the first and second characteristics that corresponds with a preferred value of the variable physiological metric. An exemplary "value" may, for example, include a specific or relative characteristic or set of characteristics of the signal or signals described in FIG. 10. Step S1040 may function to identify a value of the MSKC to CC timing relationship that causes the physiological metric to exhibit a generally more favorable or preferred value, using that identified value subsequently as representative of the target timing relationship. For example, a preferred value of a physiological metric may be a lowest average HR of the user observed under otherwise constant conditions, because the hemodynamics that result from MCP can lead to an average lowest HR for the user. The value representative of the target MSKC to CC timing relationship (i.e. the value representative of the preferred timing relationship between the first and second characteristics) might alternatively include, for example, values described by a sensed PPG signal that correlate with a particular "PPG shape", "PPG characteristic" or "PPG relative shape" without knowing exactly the timing relationship represented by that shape.

In one exemplary process that utilizes the method outlined in FIG. 10 for determining a target timing relationship, a user is provided timing prompts for performing a rhythmic activity at a generally stable work output level using, for example a treadmill such as shown in FIG. 8 and the prompting system shown in FIG. 3A. The system is configured to vary the targeted MSKC to CC timing relationship over time to expose the user to a number (at least two) of different timing relationships, and then identifies the "optimum" timing relationship that corresponds to a relatively favorable value in the measured physiologic metric. This optimum timing relationship may then be considered the "calibrated" target timing relationship for subsequent use. In an alternative embodiment, this procedure may be used to identify a measured characteristic of a signal responsive to the actual MSKC to CC timing relationship that corresponds to the relatively favorable value in the measured physiologic metric. In one example, the signal may be a PPG and the measured characteristic may be the pulse amplitude or, additionally or alternatively, a measure of the signal complexity.

In some embodiments, the method of FIG. 10 may further include providing to the user a recurrent prompt from a prompt device at a prompt rate as a timing indication for performance of the rhythmic musculoskeletal activity, such that the user's MSKC timing in response to the prompt substantially correlates with a preferred value of the physiological metric.

In some embodiments, the calibration method of FIG. 10 may be used to determine a target value representative of a preferred MSKC to CC relative timing relationship through analysis for trends in sensed MSKC to CC timing signals that occur when a user is guided by an exemplary system to readily achieve cardiolocomotor synchronization, thereby determining signal characteristics that correlate with a naturally preferred MSKC to CC relative timing relationship.

Natural cardiolocomotor synchronization may be described as "physiological MSKC to CC timing stickiness"—wherein a particular MSKC to CC timing relationship naturally preferentially occurs with the highest frequency of all possible timing relationships, due to a natural physiological tendency for many individuals towards a pump timing consistent with MCP. Physiological MSKC to CC timing stickiness may occur when the HR of the user approaches an integer multiple of the MSKR of a user. Therefore, in embodiments of the system and methods, a user is paced at a MSKR while being guided to a level of exertion at which the HR of the user approximates an integer multiple of the MSKR of the user. With the HR and MSKR substantially aligned in this manner, values representative of the MSKC to CC timing relationship are monitored and analyzed on a processor in order to identify statistically more common values representative of specific CC timing to MSKC timing that may be preferred, due to the natural tendency for physiology to trend towards a higher incidence of the physiologically more beneficial (preferred) timing relationships (e.g. timing that is consistent with MCP) and to trend away from timing relationships that are not physiologically preferable (e.g. timing that is consistent with iMCP). In another example, the system may be calibrated by monitoring the frequency of MSKC to CC timing relationships during periods of physical activity wherein the HR approaches an integer multiple of the MSKC without the user being guided. For example, certain individuals are able to naturally step with the timing of maximal MSKC arterial pumping occurring during early cardiac diastole while running and/or walking without being prompted to do so, at least for statistically significant albeit often short periods of time. In preferred embodiments of a calibration method, this stickiness is facilitated when users are provided with an MSKC timing indicator (e.g. a metronome or musical step timing prompt while running) that is constant while they are guided, to a target HR where the target HR is substantially an integer multiple of the MSKR.

In another example method for determining "stickiness", prompting a user at a rate that is slightly different than an integer multiple of the HR may be used. For example guiding the user to an MSKR (MSKCs per minute) equal to their current HR plus 1, 1.5, 2, 3, 4 or minus 1, 1.5, 2, 3, 4 per minute, may increase the likelihood of seeing the stickiness phenomenon occur over and over as the user sequentially cycles through various MSKC to CC timing relationships. The MSKC to CC timing relationship stickiness, which may be caused by a naturally occurring neural feedback loop within the cardiac tissue, typically includes a natural physiological delay that may be compensated for on a processor in calibration embodiments of the method and system. In some calibration embodiments, the system may oscillate or alter MSKC prompt timing in relationship to the user's CC timing so that the prompt guides the user back and forth across a desired MSKC to CC phase range, while the system analyzes the values of the signals for trends consistent with this physiological stickiness phenomenon. Further, the system or user may loosen the "control" in a target MSKC to CC timing relationship range in order to promote physiological stickiness. For example, automatic controls may automatically adjust an incline, speed, cadence, phase, or target HR, to bring the MSKR and HR of the user into adequate alignment to facilitate determination of the values of the sensed signals that represent the most frequent MSKC to CC relative timing of a physiological timing stickiness of the user.

Some embodiments of the system calibrate the system through identification of physiological MSKC to CC timing stickiness, while in other embodiments, one or more of the described techniques of enabling physiological stickiness may be used as a technique for guiding a user to achieve MCP. In exemplary calibration and MCP guidance embodiments, the user's work output is guided or otherwise directed towards a target HR, such that the target HR of the user equals an integer multiple of the MSKR of the user. The MSKR (cadence) of the user may be an unguided (e.g. naturally occurring) cadence, or the user may be guided by an embodiment of the system to a designated substantially constant cadence, the cadence, in either case, tied to a target HR chosen by the user or suggested by the system. In some embodiments, the work output may be modified to approach the target HR. For example, the work output may be modified by guiding the user to changes in stride length or incline during walking or running, or by altering resistance of a bicycle or aerobic exercise machine. Further, the MSK cadence may be determined by the target HR. Alternatively, the target HR may be determined by the desired cadence. In some embodiments, a combination of both desired target HR and desired cadence may be used to select an intermediate cadence and target HR.

In another embodiment of a calibration process, the user is provided with a prompt that guides the user to an MSKR that slightly differs by a constant amount from the user's HR (e.g., +1 or +1.5 or +2 or . . . per minute) so that the user's MSKC to CC timing relationship cycles, such as is seen in FIG. 6A. During this period of time (e.g., 1 to 5 minutes), the actual timing relationship S1020 and associated values of the physiologic metric S1030 are recorded. The target timing relationship is then determined according to S1040. In yet another embodiment, this process is repeated after altering the prompt to guide the user to an MSKR with an opposite constant difference to their HR (e.g., −1 or −1.5 or −2 or . . . per minute, or vice versa if the former guidance was to be slower). The final target timing relationship is then determined using the two results obtained in S1040 under the two conditions, for example the average of the two obtained target values, thus helping to compensate for time lag between the observation of the preferred value of the physiologic metric and the user's actual MSKC to CC timing relationship that enabled it.

In some embodiments, a user may prefer to be alerted when a HR and cadence (MSKR) of the user are nearly aligned, such that the user may turn on and readily engage in an MCP enabling guidance. This functionality could also be turned on automatically when MSKR is very close to an integer multiple of the HR of a user. Thus, the user may "step to the beat" or "move to the beat" only when the user's cadence and HR are already nearly aligned. In an exemplary embodiment, a PPG sensor and an accelerometer can both exist in an earbud embodiment of the invention. In this exemplary embodiment, the user could be walking down the street without thinking about stepping to the beat, when the device identifies that the HR and step rate are substantially equivalent, therefore notifies the user that stepping to the beat to achieve MCP functionality is easily available. The user may then "opt in" at any time, turning on guidance, for example music. In this example, the music may be selected from the user's music files for it's beat frequency but the beat frequency and timing may be modified, as needed, so that the beat of the music provides a timing indication that guides the user to MCP, according to the methods described above.

Embodiments described, and hence the scope of the descriptions of systems and methods below, encompass embodiments in hardware, software, firmware, or a combination thereof. It will also be appreciated that the methods, in the form of instructions having a sequence, syntax, and content, of the present disclosure may be stored on (or equivalently, in) any of a wide variety of computer-readable media such as magnetic media, optical media, magneto-optical media, electronic media (e.g., solid state ROM or RAM), etc., the form of which media not limiting the scope of the present disclosure. A computer reading said media is operable to either transfer (e.g., download) said instructions thereto and then operate on those instructions, or cause said instructions to be read from the media and operate in response thereto. Furthermore, devices (e.g., a reader) for accessing the instructions on said media may be contained within or connected directly to the computer on which those instructions operate, or may be connected via a network or other communication pathway to said computer.

Furthermore, while a plurality of exemplary embodiments have been presented in the foregoing detailed description, it should be understood that a vast number of variations exist, and these exemplary embodiments are merely representative examples, and are not intended to limit the scope, applicability or configuration of the disclosure in any way. Various of the above-disclosed and other features and functions, or alternative thereof, may be desirably combined into many other different systems or applications. Various presently unforeseen or unanticipated alternatives, modifications variations, or improvements therein or thereon may be subsequently made by those skilled in the art which are also intended to be encompassed by the present disclosure.

In addition, the methods and systems described herein guide the user in the performance of two major categories of rhythmic physical activities, namely MSK movement and skeletal muscle contraction cycles, in order to favorably coordinate peripheral vascular pumping with the heart's pumping activity. These two categories of rhythmic physical activities, together or individually, are included in the scope of the disclosure, even where only one of the two categories has been described. Therefore, for example, the descriptive phrases MSK movement, skeletal muscle contraction, skeletal muscle relaxation, MSK pumping cycles, and MSK activity should in many cases be considered included where one or more of the terms was not mentioned.

Therefore, the foregoing description provides those of ordinary skill in the art with a convenient guide for implementation of the disclosure, and contemplates that various changes in the functions and arrangements of the described embodiments may be made without departing from the spirit and scope of the disclosure.

What is claimed is:

1. A method for guiding a user towards a target rhythmic musculoskeletal activity cycle (MSKC) to cardiac cycle (CC) timing relationship, comprising:

providing a recurrent prompt from a prompt device to a user, wherein the recurrent prompt is provided to guide the user to time performance of a rhythmic musculoskeletal activity with the recurrent prompt;

detecting a first signal responsive to the CC of the user using a first sensor;

determining, with a processor, a CC rate of the user from the first signal;

detecting a second signal responsive to the MSKC of the user using the first sensor or a second sensor;

identifying, with a processor, a target MSKC-to-CC timing relationship;

determining, with a processor, an actual MSKC-to-CC timing relationship between the CC and the MSKC;

comparing, with a processor, the actual MSKC-to-CC timing relationship to the target MSKC-to-CC timing; and adjusting the recurrent prompt based on a difference between the actual MSKC-to-CC timing relationship and the target MSKC-to-CC timing relationship so as to guide the user to reduce the magnitude of the difference.

2. The method of claim 1, wherein identifying a target MSKC-to-CC timing relationship is selected from a group consisting of: calculating a target MSKC-to-CC timing relationship, obtaining a target MSKC-to-CC timing relationship from a table, and identifying a pre-programmed value.

3. The method of claim 2, wherein calculating a target MSKC-to-CC timing relationship at least partially comprises one or more of: using a pre-programmed algorithm or table that utilizes at least one measurement of the physiology of the user, using a pre-programmed algorithm or table that references a heart rate of the user, using a pre-programmed algorithm or table that references information obtained from an ECG signal of the user, using a prior calibration of an optical target timing of the user, and using a pre-programmed algorithm or table responsive to the sex of the user.

4. The method of claim 1, wherein adjusting the recurrent prompt comprises one or more of adjusting a rate of the recurrent prompt, adjusting a timing of the recurrent prompt, and adjusting a sound of the recurrent prompt.

5. The method of claim 4, wherein adjusting the sound of the recurrent prompt comprises one or more of changing a: volume, pitch, or one or more musical attributes of the recurrent prompt.

6. The method of claim 1, wherein providing the recurrent prompt from the prompt device to a user comprises playing a song having a recurrent beat.

7. The method of claim 6, wherein adjusting the recurrent prompt comprises automatically selecting a new song from a playlist, wherein the new song has a preferred beat frequency that is closer to the beat frequency of the sensed MSKC frequency.

8. The method of claim 6, wherein adjusting the recurrent prompt comprises adjusting a playback speed of the song to fine-tune timing of the recurrent beat.

9. The method of claim 6, wherein adjusting the recurrent prompt comprises one or more of changing a volume of the recurrent beat in the song relative to a remainder of the song, changing the pitch of the recurrent beat, and changing the musical quality of the recurrent beat within the song in response to a change in an accuracy or consistency of achieving the target MSKC-to-CC timing relationship.

10. The method of claim 6, wherein adjusting the recurrent prompt comprises one or more of: changing a volume of an additional recurrent beat on top of the song relative to a remainder of the song, changing the pitch of the additional recurrent beat, and changing the musical quality of the additional recurrent beat within the song in response to a change in an accuracy or consistency of achieving the target MSKC-to-CC timing relationship.

11. The method of claim 1, wherein the steps of:
identifying the target MSKC-to-CC timing relationship,
determining the actual MSKC-to-CC timing relationship between the CC and the MSKC, and
comparing the actual MSKC-to-CC timing relationship to the target MSKC-to-CC timing,
are performed by a single processor or by a plurality of processors.

12. The method of claim 1, wherein adjusting the recurrent prompt comprises adjusting a prompt rate of the recurrent prompt such that the CC rate is an integer multiple of the prompt rate.

13. The method of claim 1, wherein determining the CC rate of the user from the first signal comprises identifying one or mote features of the first signal that repeat once per CC, and identifying a rate at which the one or more features repeat, wherein the one or more features correspond to one or more of: an ECG R-wave, an ECG T-wave, an end of the ECG T-wave, a peak of a cardiovascular systolic pressure, a nadir of a diastolic cardiovascular pressure, and a transition point in a cardiovascular pressure of the user.

14. A system for guiding a user towards a target rhythmic musculoskeletal activity cycle (MSKC) to cardiac cycle (CC) timing relationship, comprising:
a user guidance interface configured to provide a recurrent prompt to a user, wherein the recurrent prompt is provided to guide the user to time performance of a rhythmic musculoskeletal activity with the recurrent prompt;
a first sensor configured to sense a first signal responsive to the CC;
a second sensor configured to sense a second signal responsive to the MSKC of the user; and
at least one processor communicatively coupled to the first sensor, the second sensor, and the user guidance interface, the at least one processor configured to:
receive the first signal from the first sensor;
receive the second signal from the second sensor;
determine a CC rate of the user from the first signal;
identify a target MSKC-to-CC timing relationship;
determine an actual MSKC-to-CC timing relationship between the CC and the MSKC;
compare the actual MS KC-to-CC timing relationship to the target MSKC-to-CC timing; and
command the user guidance interface to adjust the recurrent prompt based on a difference between the actual MSKC-to-CC timing relationship and the target MSKC-to-CC timing relationship so as to guide the user to reduce the magnitude of the difference.

15. The system of claim 14, wherein the first sensor signal comprises at least one of an electrocardiogram (ECG) and a plethysmogram.

16. The system of claim 14, wherein the first sensor is positionable on an arm, on a finger, around an ear lobe, in an ear canal, on a forehead, or over an eye.

17. The system of claim 14, wherein the second sensor comprises at least one of an accelerometer, an electromyographic sensor, a pressure sensor, a switch, a camera, a gryroscope, a proximity sensor, and a plethysmographic sensor.

18. The system of claim 14, wherein the user guidance interface is configured to play music to the user.

19. The system of claim 18, wherein the recurrent prompt is an audible prompt that comprises a beat of a musical track.

20. The system of claim 19, wherein a volume of the beat comprising the recurrent prompt is controlled separately from a volume of a remainder of the musical track based on at least one of a user setup configuration, a program setup configuration, a consistency of the user in stepping to the recurrent prompt, or an accuracy of the user stepping with the recurrent prompt.

21. The system of claim 14, wherein the at least one processor comprises a plurality of processors, and wherein each of the plurality of processors is configured to perform one or more functions.

22. The system of claim 14, wherein some of or all the system is wearable and positioned on or in one or more of a: chest strap, helmet, headband, hat, visor, sports bra, watch, wristband, armband, ankle band, headset, earbud, glasses, goggles, or patch.

* * * * *